(12) United States Patent
Holakovsky et al.

(10) Patent No.: US 8,950,393 B2
(45) Date of Patent: Feb. 10, 2015

(54) NEBULIZER

(75) Inventors: Holger Holakovsky, Ingelheim am Rhein (DE); Florian Witte, Ingelheim am Rhein (DE); Frank Herrmann, Ingelheim am Rhein (DE); Charles William Sears, Boxford, MA (US); Christopher Michael Catinella, Marlboro, MA (US); Mario Alberto Gonzalez, Somerville, MA (US); Sean Landis Philips, S. Lancaster, MA (US); Paul Bertram, Franklin, MA (US); Marc Rohrschneider, Ingelheim am Rhein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 245 days.

(21) Appl. No.: 13/477,527

(22) Filed: May 22, 2012

(65) Prior Publication Data
US 2013/0056888 A1    Mar. 7, 2013

Related U.S. Application Data

(63) Continuation of application No. PCT/US2011/037527, filed on May 23, 2011.

(51) Int. Cl.
*A61M 11/00* (2006.01)
*A61M 15/00* (2006.01)
*A61M 11/08* (2006.01)

(52) U.S. Cl.
CPC ........... *A61M 15/0065* (2013.01); *A61M 11/08* (2013.01); *A61M 11/007* (2014.02); *A61M 15/0073* (2014.02); *A61M 15/0081* (2014.02); *A61M 15/0028* (2013.01);

(Continued)

(58) Field of Classification Search
USPC .......................... 128/200.14, 200.17, 200.21
See application file for complete search history.

(56) References Cited

U.S. PATENT DOCUMENTS

| 5,833,088 A | 11/1998 | Kladders et al. |
| 7,665,461 B2 * | 2/2010 | Zierenberg et al. ...... 128/200.21 |

(Continued)

FOREIGN PATENT DOCUMENTS

| WO | 96/06011 A2 | 2/1996 |
| WO | 2006125577 A2 | 11/2006 |

(Continued)

OTHER PUBLICATIONS

Internatinal Search Report for International Application No. PCT/US2011/037527 Dated Apr. 4, 2012.

*Primary Examiner* — Robert A Hopkins
(74) *Attorney, Agent, or Firm* — Roberts Mlotkowski Safran & Cole, P.C.; David S. Safran

(57) ABSTRACT

A nebulizer which has an insertable container and a counter device for counting operations of the nebulizer, and is opened for replacing the container. A securing device having locking portions which are forced apart is provided to prevent reconnection of an already used container. The nebulizer has an indicator for showing the current container number and/or symbols indicating the need container replacement. The indicator is driven by the force of an internal spring. The indicator member also controls a lock of the container for locking the container against further actuation. The lock is reset after container replacement.

59 Claims, 13 Drawing Sheets

(52) U.S. Cl.
CPC . *A61M 2202/0468* (2013.01); *A61M 2205/273* (2013.01); *A61M 2205/276* (2013.01); *A61M 2205/6036* (2013.01)
USPC ............ 128/200.14; 128/200.17; 128/200.21

(56) References Cited

U.S. PATENT DOCUMENTS

| | | | |
|---|---|---|---|
| 8,387,614 B2* | 3/2013 | Geser et al. ............ | 128/200.14 |
| 2002/0129812 A1 | 9/2002 | Litherland et al. | |
| 2003/0140921 A1 | 7/2003 | Smith et al. | |
| 2003/0178020 A1 | 9/2003 | Scarrott | |
| 2005/0087191 A1 | 4/2005 | Morton et al. | |
| 2006/0237009 A1 | 10/2006 | Jones et al. | |
| 2007/0107720 A1 | 5/2007 | Boeck et al. | |
| 2007/0186923 A1 | 8/2007 | Poutiatine et al. | |
| 2008/0173669 A1 | 7/2008 | Pocock et al. | |
| 2009/0235924 A1 | 9/2009 | Holakovsky et al. | |
| 2011/0011393 A1 | 1/2011 | Geser et al. | |

FOREIGN PATENT DOCUMENTS

| | | |
|---|---|---|
| WO | 2007/022898 A2 | 3/2007 |
| WO | 2009/115200 A1 | 9/2009 |

* cited by examiner

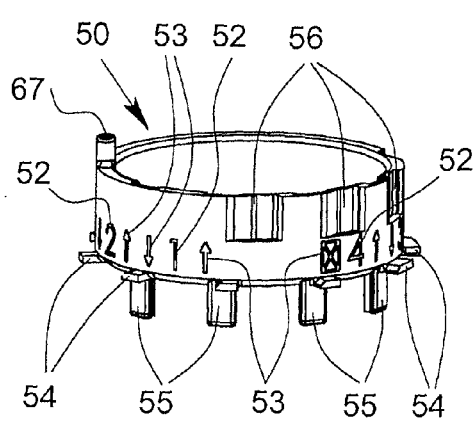
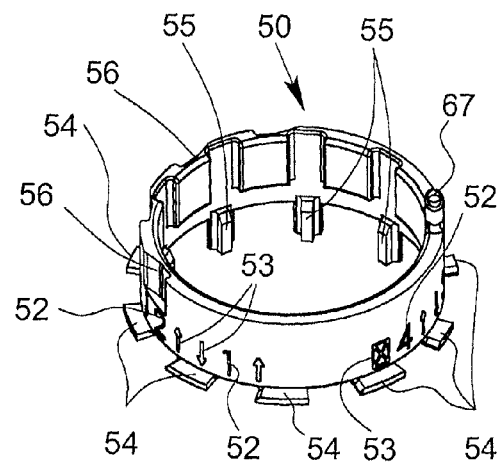
Fig. 12
Fig. 13
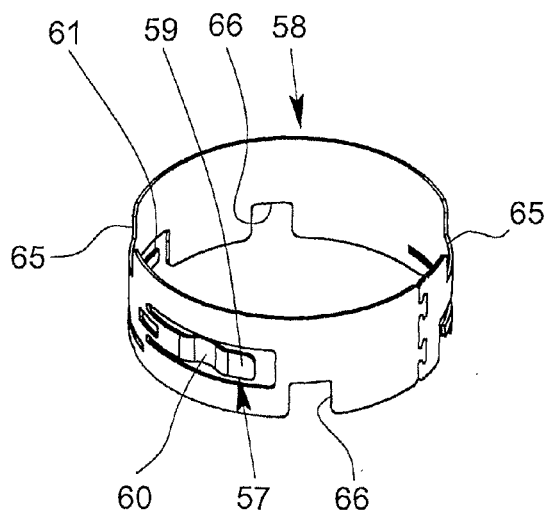
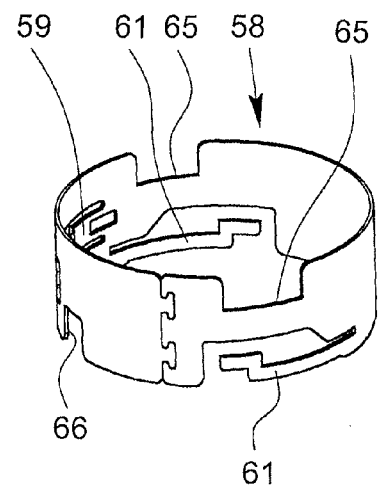
Fig. 14
Fig. 15

NEBULIZER

CROSS REFERENCE TO RELATED APPLICATION

This application is a continuation of International Patent Application No. PCT/US2011/037527 which designates the United States.

BACKGROUND OF THE INVENTION

1. Field of the Invention

The present invention relates to a nebulizer for nebulizing a fluid.

2. Description of Related Art

International Patent Application Publication WO 2006/125577 A2 discloses a nebulizer which comprises, as a reservoir for fluid which is to be atomized or nebulized, an insertable rigid container having an inner bag containing the fluid and a pressure generator with a drive spring for delivering and atomizing the fluid. The container is pre-installed in nebulizer in a delivery state. The pre-installed container is held by a transportation lock unmovable within the housing in the delivery state in order to avoid any undesired opening of the container. Before being used for the first time a lower housing part of the nebulizer is completely closed. Thus, the pre-installed container is opened by a delivery tube piercing a sealing and a septum to fluidically connect to the inner bag of the container. Further, the transportation lock is opened so that the container can move inside the nebulizer back and forth.

By rotating the lower housing part the drive spring can be put under tension and fluid can be sucked into a compression chamber of the pressure generator. Simultaneously, the container is moved into the lower housing part in a stroke movement within the nebulizer and when tensioned for the first time the container may be pierced through its base by a piercing element in the lower housing part to allow venting of the container. After manual operation of a blocking element the drive spring is released and moves the delivery tube into the pressure chamber so that the fluid is put under pressure by the drive spring and is delivered or atomized through a nozzle into a mouthpiece as an aerosol, without the use of propellant gas.

International Patent Application Publication WO 2007/022898 A2 disclose a similar nebulizer. A container can be inserted into a housing of the nebulizer. The housing is closed by a lower housing part. The container is moving axially forth and back during conveying of the fluid to be nebulized, and during pressure generation and nebulization. A counter device can be arranged in the lower housing part. The counter device locks the nebulizer against further use if a predetermined number of operations has been reached or exceeded. Then, the housing part may be replaced together with the counter device and the container. The container may be connected inseparably with the housing part. Further, the nebulizer comprises a device for permanently locking the nebulizer when a certain number of containers have been used or when a certain number of operations have been reached. Coding can be provided so that only the right or permitted housing part can be coupled to the upper part of the nebulizer. A first coding element is arranged at the upper part and a complementary coding element, in particular an axial groove, is provided in the housing part.

SUMMARY OF THE INVENTION

A primary object of the present invention is to provide a nebulizer allowing easy and/or improved handling and to provide an improved or universal coding.

The above object is achieved by a nebulizer as described herein.

A first aspect of the present invention is that the nebulizer comprises an indicator member showing the number of containers that have been used or can still be used, and showing in addition symbols indicating container replacement. The numbers and symbols are shown alternately by the indicator. This allows easy or improved handling or use of the nebulizer.

According to another aspect of the present invention, the nebulizer comprises an indicator member showing the number of containers that have been used or still can be used and/or the number of operations that have been performed or still can be performed with this nebulizer, wherein the indicator member is moved or rotated stepwise, i.e., indexed, or more generally driven, by the force of a spring. This allows easy and/or improved handling or use of the nebulizer. In particular, any additional manual force to drive the indicator member or to use the nebulizer can be avoided. Instead, the spring is used preferably as an energy store to drive the indicator member and/or a lock of the nebulizer.

According to a further aspect of the present invention, the indicator member drives or controls a lock of the nebulizer such that the nebulizer is locked against further use in a first locked state when the container is replaced, wherein the first locked state is reset by indexing the indicator member and/or resetting the lock when the container has been replaced. This allows easy and/or improved handling or construction of the nebulizer as the indicator member controls the lock.

In general, the indicator member is preferably ring-like. This allows a very simple and/or compact construction.

Preferably, the indicator member works or shows said numbers and/or symbols mechanically. This allows a very robust or simple construction of the nebulizer.

According to another aspect of the present invention, the nebulizer comprises a lock for locking the nebulizer against further use in a first locked state when the container is replaced, wherein the locked state is reset by resetting the lock when the container has been replaced, and comprises further a control member for controlling or driving the lock, wherein the control member is moved or rotated stepwise, with other words indexed, or more generally driven, by the force of a spring. This allows easy and/or improved handling or use of the nebulizer. In particular, any manual force or the like can be avoided to drive the control member and to actuate the lock. Instead, the force of the spring is used as an energy source.

According to a further aspect of the present invention, the lock and/or first locked state is blocked in a second blocked state against resetting if a predetermined number of containers has been used. Thus, the lock can be used not only for locking the nebulizer in the first locked state (which is reversible when the container is replaced) but also for locking the nebulizer in the second locked state (final locked state or life span blocking), which cannot be reversed anymore. This double-function allows easy or improved handling or use of the nebulizer as the construction of the nebulizer can be simplified and/or made very secure.

Preferably, the lock locks the nebulizer in the locked state against conveying of fluid into a pressure generator and/or against tensioning of a drive spring of the nebulizer. This allows easy and/or improved handling of the nebulizer, in particular as it allows intuitive handling of the nebulizer.

Preferably, the control member or lock locks the nebulizer or its housing part against opening or container replacement before the first locked state has been reached and/or in the second locked state. Thus, early opening of the nebulizer and early container replacement can be avoided. Further, opening of the nebulizer and container replacement can be prevented in the irreversible final locked state, i.e., in the second locked state. This facilitates intuitive handling. Further, it can be prevented that the nebulizer is opened before the respective container has been (sufficiently) used or has been emptied. Thus, potential soiling of inner parts of the nebulizer can be minimized and/or a defined handling can be secured.

According to another aspect of the present invention, the nebulizer comprises a securing device associated to a replaceable container of the nebulizer, wherein the securing device prevents that the associated container can be connected or used with the nebulizer once more after it has already been used with the nebulizer, wherein the securing device comprises locking portions, in particular arms, which force apart and/or move radially when the container is or has been connected to or with nebulizer for the first time and/or after the used container has been detached from the nebulizer such that the use container cannot be connected or used the nebulizer once more. This allows easy and/or improved handling of the nebulizer. In particular, it allows a very secure and simple construction.

According to another aspect of the present invention, the nebulizer comprises a housing part which holds the container inseparably and which can be attached to the nebulizer for connecting the container to the nebulizer, wherein the housing part comprises a coding such that the housing part can be attached to the nebulizer and the container can be connected to the nebulizer only if the coding matches with a coding formed at the nebulizer or an inner part of the nebulizer. Preferably, the coding is formed at the housing part by one or more coding elements that can be attached to the housing part by clipping and/or inserting. Preferably, the coding is formed at the nebulizer or inner part by a retaining part provided with one or more coding portions, wherein the retaining part is connected to the nebulizer or inner part by clipping and/or inserting. This allows a very simple realization and adaptation of the coding so that only certain housing parts and containers can be used with a nebulizer.

The above aspects of the present invention and the further aspect described below can be realized independently from each other, and in any combination.

Further advantages, features, characteristics and aspects of the present invention will become apparent from the following detailed description of preferred embodiments with reference to the accompanying drawings.

BRIEF DESCRIPTION OF THE DRAWINGS

FIG. 12 is a side view of a control/indicator member of the nebulizer according to FIG. 6;

FIG. 13 is a perspective view of the control/indicator member according to FIG. 12;

FIG. 14 is a perspective side view of a lock member of the nebulizer according to FIG. 6;

FIG. 15 is another perspective view of the lock member according to FIG. 14.

DETAILED DESCRIPTION OF THE INVENTION

Figure 1:
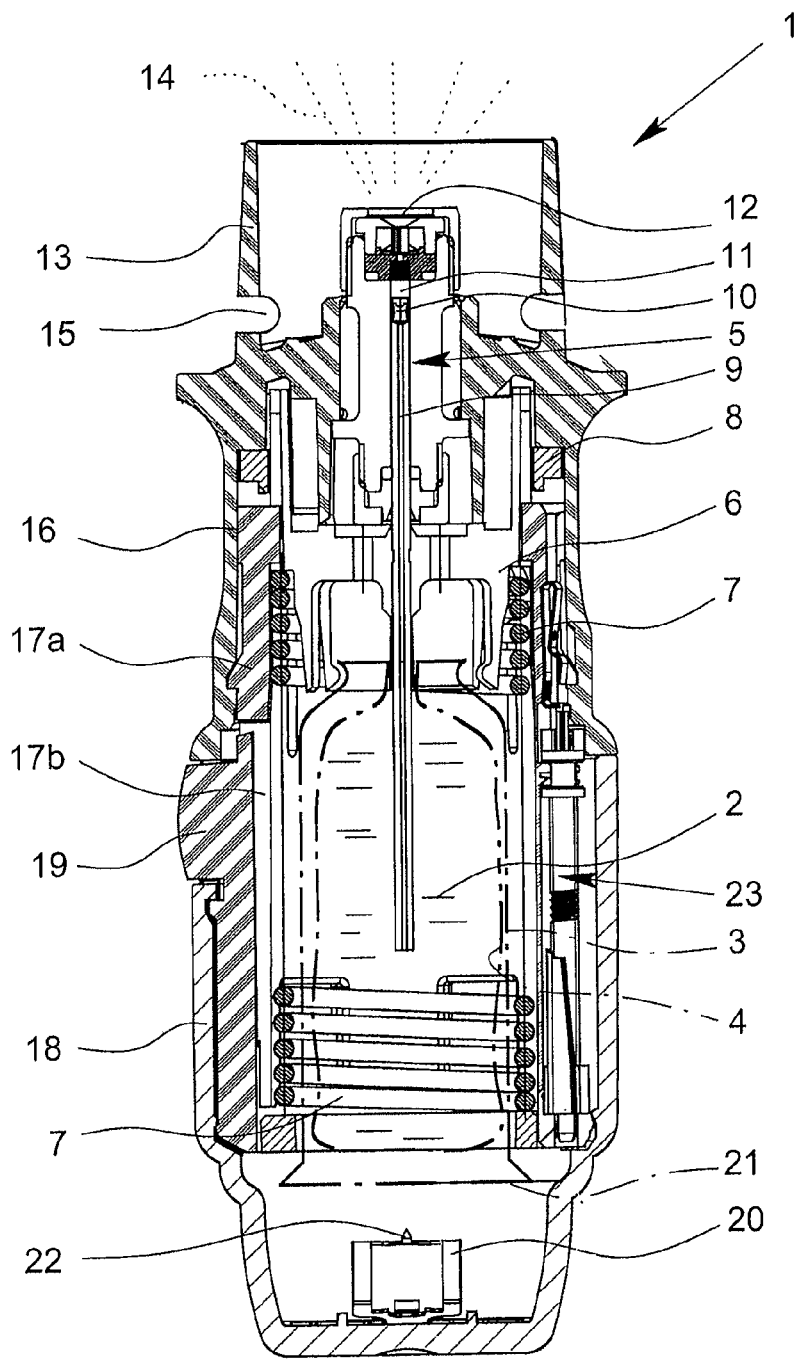
FIG. 1 is a schematic section of a known nebulizer in a relaxed state.

In the Figures, the same reference numerals are used for identical or similar parts, resulting preferably in corresponding or comparable properties and advantages, even if the associated description is not repeated.

Figure 2:
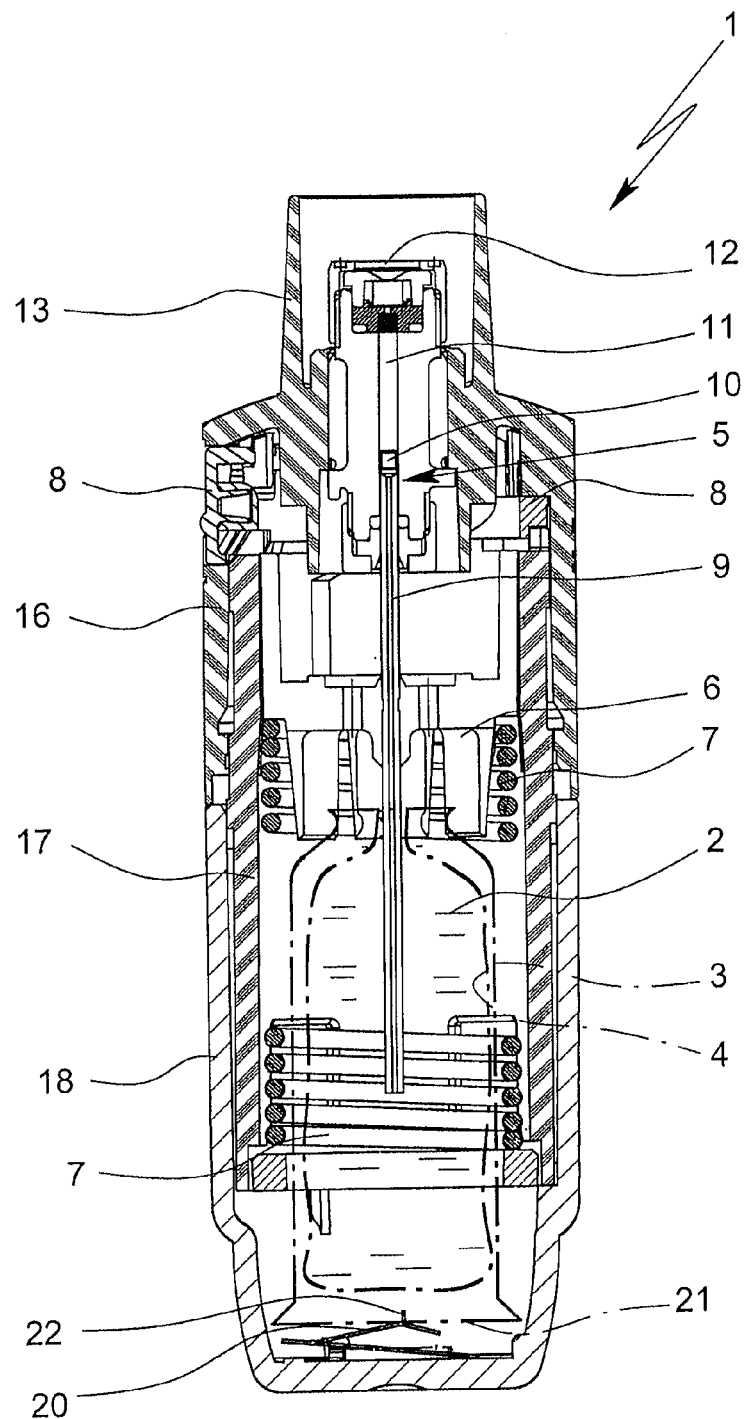
FIG. 2 is a schematic section, rotated 90° compared with FIG. 1, of the known nebulizer in a tensioned state.

FIGS. 1 & 2 show a known nebulizer 1 for atomizing a fluid 2, particularly a highly effective pharmaceutical composition, medicament or the like, diagrammatically shown in a untensioned, i.e., relaxed, state (FIG. 1) and in a tensioned state (FIG. 2). The nebulizer 1 is constructed in particular as a portable inhaler and preferably operates only mechanical and/or without propellant gas.

When the fluid 2, preferably a liquid, more particularly a pharmaceutical composition, is nebulized, an aerosol 14 (FIG. 1) is formed, which can be breathed in or inhaled by a user. Usually, the inhaling is done at least once a day, more particularly, several times a day, preferably at set intervals, depending on the complain or illness from which a patient is suffering.

The nebulizer 1 is provided with or comprises an insertable or replaceable container 3 containing the fluid 2. The container 3 thus forms a reservoir for the fluid 2, which is to be nebulized. Preferably, the container 3 contains multiple doses of fluid 2 or active substance in particular sufficient to provide up to 200 dosage units or doses, for example, i.e., to allow up to 200 sprays or applications. A typical container 3, as disclosed in International Patent Application Publication WO 96/06011 A1 and corresponding U.S. Pat. No. 5,833,088, holds e.g., a volume of about 2 to 20 ml.

It is noted that the dose can vary, in particular depending on the fluid 2 or medicament. The nebulizer 1 can be adapted respectively.

Further, the number of doses contained in the container 3 and/or the total volume of the fluid 2 contained in the container 3 can vary depending on the fluid 2 or respective medicament and/or depending on the container 3 and/or depending on the necessary medication or the like.

Preferably, the container 3 can be replaced or exchanged, wherein the number of containers 3, which can be used with the same nebulizer 1, is preferably restricted, e.g., to a total number of four or five containers 3.

The container 3 is preferably substantially cylindrical or cartridge-shaped and once the nebulizer 1 has been opened the container 3 can be inserted therein preferably from below and changed if desired. It is preferably of rigid construction, the fluid 2 in particular being held in a collapsible bag 4 in the container 3.

The nebulizer 1 preferably comprises a pressure generator 5 for conveying and nebulizing the fluid 2, particularly in a preset and optionally in an adjustable dosage amount. The nebulizer or pressure generator 5 preferably comprises a holder 6 for releasably holding the container 3, a drive spring 7 associated to the holder 6, only partly shown, and/or a blocking element 8 preferably in form of or with a button for preferably manual actuation or depressing, which blocking element 8 can catch and block the holder 6 and can be manually operated to release the holder 6 allowing drive spring 7 to expand. The nebulizer 1 or pressure generator 5 preferably comprises further a conveying element, such as a conveying tube 9, a non-return valve 10, a pressure chamber 11 and/or an nozzle 12 for nebulizing the fluid 2 into a mouthpiece 13. The completely inserted container 3 is fixed or held in the nebulizer 1 via the holder 6 such that the conveying tube 9 penetrates into the container 3. The holder 6 is preferably constructed so that the container 3 can be exchanged.

When the drive spring 7 is axially tensioned in the tensioning process the holder 6 with the container 3 and the conveying tube 9 are moved downwards in the drawings and fluid 2 is sucked out of the container 3 into the pressure chamber 11 of the pressure generator 5 through the non-return valve 10. In this state, the holder 6 is caught by the blocking element 8 so that the drive spring 7 is kept compressed. Then, the nebulizer 1 is in the so-called activated or tensioned state.

During the subsequent relaxation in the nebulization process, after actuation or pressing of the blocking element 8, the fluid 2 in the pressure chamber 11 is put under pressure as the conveying tube 9 with its now closed non-return valve 10 is moved back in the pressure chamber 11, here in the drawings upwards, by the relaxation or force of the drive spring 7 and now acts as a pressing ram or piston. This pressure forces the fluid 2 through the nozzle 12, whereupon it is nebulized into the aerosol 14, as shown in FIG. 1.

Generally, the nebulizer 1 operates with a spring pressure of 5 to 200 MPa, preferably 10 to 100 MPa on the fluid 2, and/or with a volume of fluid 2 delivered per stroke of 10 to 50 μl, preferably 10 to 20 μl, most preferably about 15 W. The fluid 2 is converted into or nebulized as aerosol 14, the droplets of which have an aerodynamic diameter of up to 20 μm, preferably 3 to 10 μm. Preferably, the generated jet spray has an angle of 20° to 160°, preferably 80° to 100°. These values also apply to the nebulizer 1 according to the teaching of the present invention as particularly preferred values.

A user or patient (not shown) can inhale the aerosol 14, preferably while an air supply can be sucked into the mouthpiece 13 through at least one optional air supply opening 15.

Preferably, the nebulizer 1 or drive spring 7 can be manually activated or tensioned, in particular by actuation of an actuation member.

The nebulizer 1 preferably comprises an upper housing part 16 and an inner part 17 which is rotatable relative thereto (FIG. 2) having an upper part 17*a* and a lower part 17*b* (FIG. 1), while an, in particular, manually operable (lower) housing part 18 is releasable fixed, particularly fitted or held onto the inner part 17, preferably by means of a retaining element 19. Preferably, the housing parts 16, 18 form a housing of the nebulizer 1. In order to insert and/or replace the container 3 the housing can be opened and/or the housing part 18 can be detached from the nebulizer 1 or its housing.

The actuation member, preferably the housing part 18, can be actuated, here rotated relative to the upper housing part 16, carrying with it or driving the inner part 17. As a result the drive spring 7 is tensioned in the axial direction by means of a gear or transmission (not shown) formed between the inner part 17, in particular its upper part 17*a*, and the holder 6 and acting on the holder 6. During tensioning, the container 3 is moved axially downwards until the container 3 assumes an end position as shown in FIG. 2. In this activated or tensioned state the drive spring 7 is under tension and can be caught or held by the blocking member 8. During the nebulizing process the container 3 is moved back into its original position (non-tensioned position or state shown in FIG. 1) by the drive spring 7. Thus, the container 3 executes a lifting or stroke movement during the tensioning process and during the nebulizing process.

The housing part 18 preferably forms a cap-like lower housing part and fits around or over a lower free end portion of the container 3. As the drive spring 7 is tensioned the container 3 moves with its end portion (further) into the housing part 18 or towards the end face thereof, while an aeration means, such as an axially acting spring 20 arranged in the housing part 18, comes in contact with base 21 of the container 3 and pierces the container 3 or a base seal thereon with a piercing element 22 when the container 3 makes contact with it for the first time, to allow air in or aeration.

The nebulizer 1 preferably comprises a counter device 23, which counts the actuations of the nebulizer 1, preferably by detecting its tensioning or the rotation of the inner part 17 relative to the upper part 16 of the housing. Preferably, the counter device 23 or an associated lock locks the (further) actuation or use of the nebulizer 1, e.g., blocks further rotation of the housing part 18/inner part 17 and, thus, tensioning of the nebulizer 1 or its drive spring 7 and/or blocks actuation of the blocking element 8, when a certain number of actuations or operations or discharged doses has been reached or exceeded.

A preferred construction and mode of operation of the inhaler or nebulizer 1 will now be described in more detail with reference to FIGS. 3 to 5, but emphasizing only essential differences from the nebulizer 1 according to FIGS. 1 & 2. The remarks relating to FIGS. 1 & 2 thus apply preferably accordingly or in a similar manner, while any desired combinations of features of the nebulizer 1 according to FIGS. 1 & 2 and the nebulizer 1 described below are possible.

Preferably, the container 3 is pre-installed. This can be realized in particular as shown in International Patent Application Publication WO 2006/125577 A2 and corresponding U.S. Patent Application Publication 2007/107720 A1, or as described in the following.

FIG. 3 shows the nebulizer 1 in a delivery state with preferably pre-installed container 3, which is still closed. In this state, the housing of the nebulizer 1 is not completely closed, in particular the housing part 18 is not completely pushed on the inner part 17. FIGS. 4 & 5 show the nebulizer 1 in an activated state with the housing completely closed and with the container 3 opened. In FIG. 4, the nebulizer 1 or drive spring 7 is tensioned, i.e., the container 3 is in its lower position. FIG. 5 shows the nebulizer 1 in a non-tensioned state, e.g., after dispensing or nebulizing of one dose of the fluid 2; the container 3 is in its upper position.

The container 3 comprises a fluid outlet 24 for outputting the fluid 2 to be dispensed. In particular, the fluid outlet 24 allows a fluidic connection between the container 3 or its bag 4, on one hand, and the nebulizer 1, its pressure generator 5 or the conveying element on the other hand.

The fluid outlet 24 has an inner closure 25 that is preferably formed by a septum, a membrane, a plastic seal or the like and/or is provided inside the container 3. Optionally, a second or outer closure 26 can be provided such that successive opening is possible by means of one common element, in particular the conveying element or conveying tube 9 or the like, and/or by piercing.

Preferably, the first or inner closure 25 is formed or supported by a closure part 27 extending from the outlet or head end of the container 3 into the container 3 or bag 4. The second or outer closure 26 is preferably located adjacent to the head or axial end of the container 3 and/or held or connected to a flange 28, which can be formed by the closure part 27 or any other suitable part. However, other constructional solutions are possible.

Figure 3:
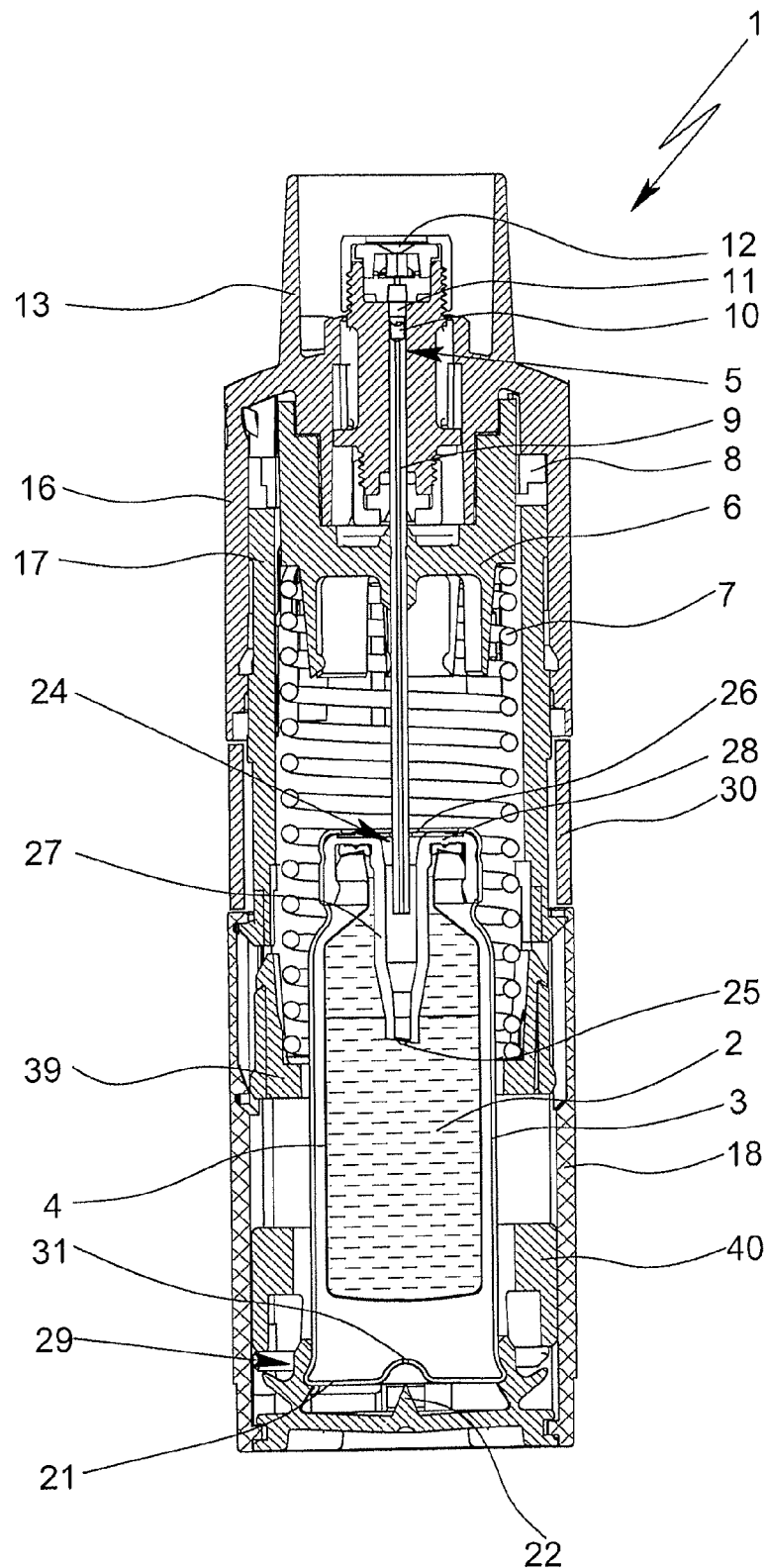
FIG. 3 is a schematic section of a nebulizer in a delivery state with a partly closed housing and with a pre-installed, closed container.
Figure 4:
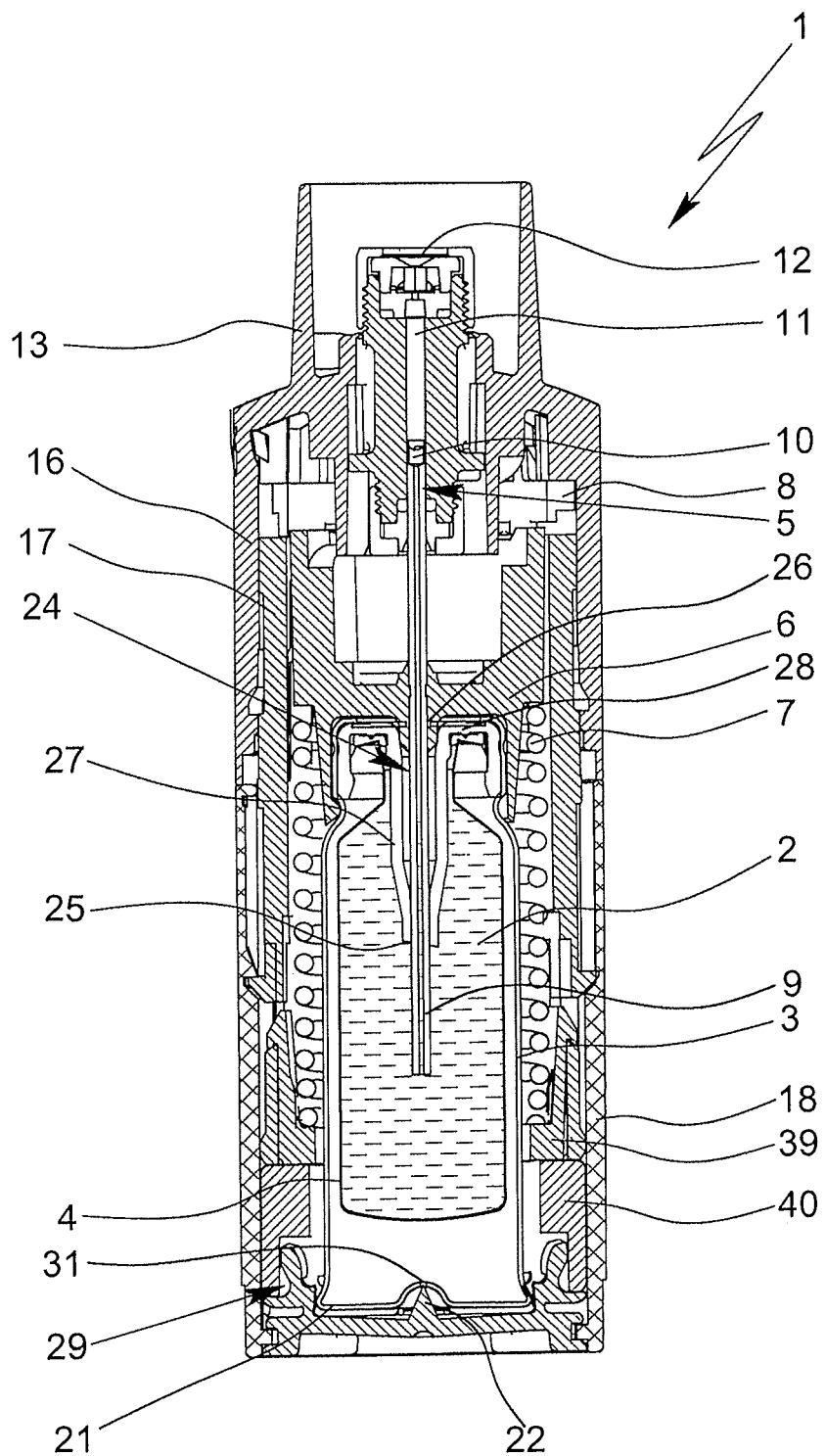
FIG. 4 is a schematic section of the nebulizer according to FIG. 3 in an activated, tensioned state with completely closed housing and with opened container.
Figure 5:
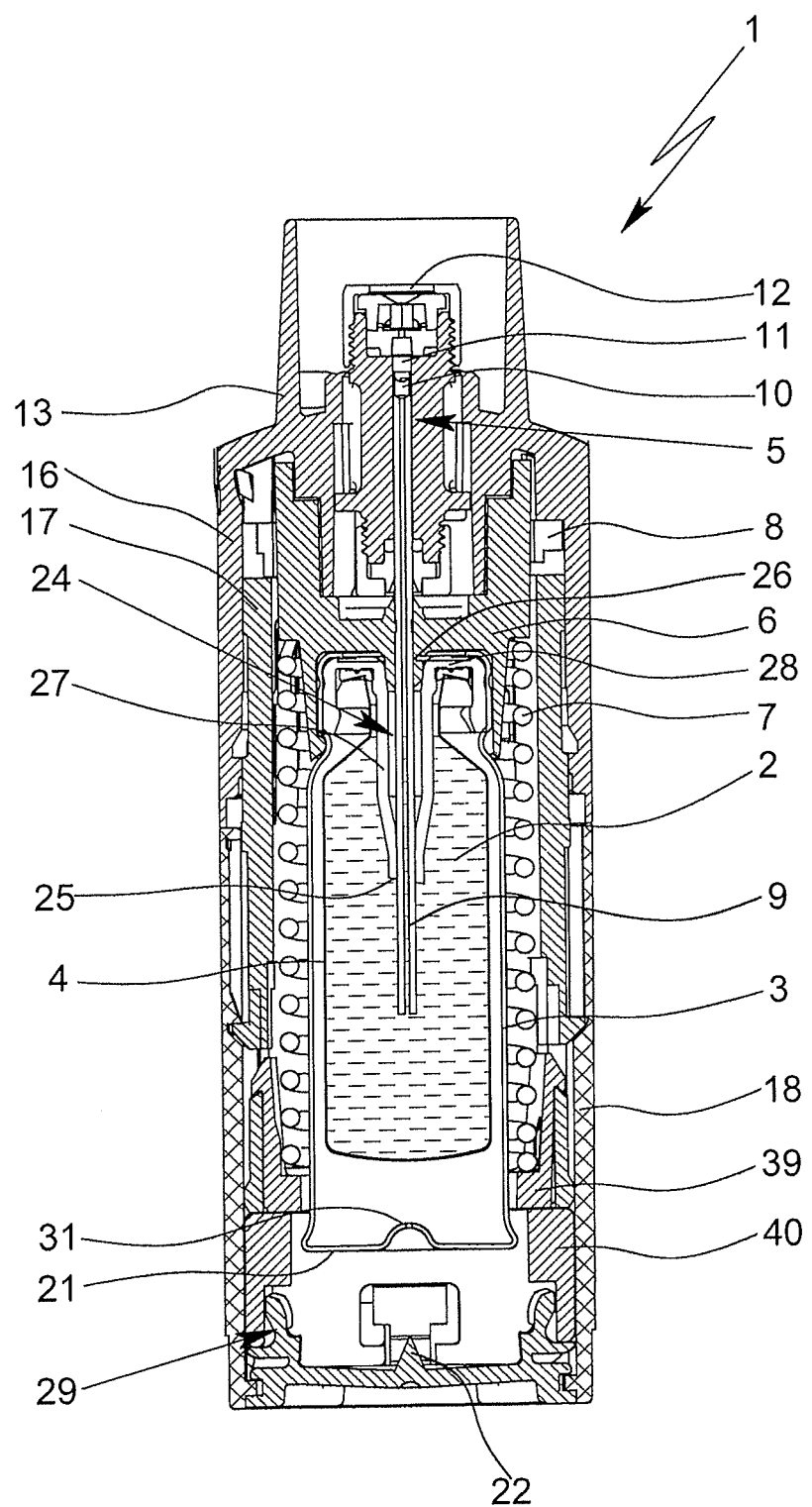
FIG. 5 is a schematic section of the nebulizer according to FIG. 4 in a relaxed state.

In the delivery state according to FIG. 3, the container 3 has been pre-installed, i.e., inserted into the nebulizer 1. However, the container 3 or its fluid outlet 24 is not yet opened. In particular, the second closure 26 is already opened, but not the first closure 25. This is achieved in particular in that the housing of the nebulizer 1 is closed only partly, i.e., not completely, in the delivery state.

In particular, the container 3 is attached to or held by or secured in the housing part 18, in particular by a transportation lock 29, which is preferably arranged within or at the housing part 18. The transportation lock 29 holds the container 3 preferably temporarily, in particular before attaching the housing part 18 to the nebulizer 1 and/or in the delivery state. In particular, the transportation lock 29 holds the container 3 fixed during the fluidic connection of container 3 and/or during the mechanic connection of container 3, here with holder 6. Preferably, the transportation lock 29 holds the container 3 fixed during opening, in particular piercing, the container 3.

In the delivery state, in which the nebulizer 1 can be shipped or delivered to the user or is still packed, the nebulizer 1 or the housing part 18 is preferably secured, in particular by means of a securing member 30, e.g., a banderole, such that the container 3 and/or housing part 18 are held sufficiently spaced from the nebulizer 1 or upper housing part 16 and/or prevented from being completely closed or completely inserted or pushed on the conveying element or tube 9, the housing or inner housing part 17 or the like and/or such that (complete) opening of the container 3, namely of the first closure 25, is prevented.

Once the security member 30 has been removed a user (not shown) can push the housing part 18 fully on in the axial direction and thereby open the container 3, i.e., first closure 25, by inserting the conveying element or conveying tube 9. FIGS. 4 and 5 show this activated state with the housing part 18 pushed fully on and/or the container 3 open (fluidically connected to the nebulizer 1 or its pressure generator 5 or the conveying element or tube 9).

FIG. 4 shows the nebulizer 1 or container 3 in the activated state, the container 3, i.e., first closure 25, is open, i.e., the container 3 or its fluid 2 is fluidically connected to the nebulizer 1 or its pressure generator 5, and the housing part 18 has been pushed fully on in the axial direction. In order to bring the holder 6 into (complete) engagement with the container 3 at the head end and then be able to move the container 3 back and/or forth for the suction/tensioning and pressing strokes, it may be necessary to tension the nebulizer 1 or it drive spring 7 for the first time. During this tensioning process, the holder 6 is moved together with the conveying tube 9 axially towards or into the housing part 18, thus bringing the holder 6 into (complete) engagement with the container 3 and preferably also moving or pressing the container 3 against the piercing element 22 in the region of the base of the housing part 18 and thereby piercing or opening a venting hole 31 in the container base 21. FIG. 4 shows the nebulizer 1 in this tensioned and activated state. The holder 6 is engaged with the container 3 and the conveying tube 9 has been fully inserted into the container 3.

FIG. 5 shows the nebulizer 1 in the relaxed, untensioned state, i.e., after atomization or discharge of a dose of the fluid 2. The holder 6 and the container 3 are in the upper position. The holder 6 is still engaged with the container 3 and remains engaged during the further uses of the nebulizer 1. Further, the container 3 is still open and fluidically connected, i.e., the nebulizer 1 remains activated.

To prevent unwanted opening of the container 3, particularly of the first closure 25, in the delivery state of the nebulizer 1, and/or to prevent (axial) movement of the container 3 relative to the associated housing part 18 before complete closing of the nebulizer 1, preferably the transportation lock 29 is provided. By frictional, forcible or interlocking engagement, for example, the transportation lock 29 prevents the container 3 from undesirably moving axially.

Preferably, the opening of the transportation lock 29 occurs automatically when closing the nebulizer 1 or its housing completely, i.e., when snapping or pushing on the housing part 18 completely towards the upper housing part 16. During this (preferably linear, axial or telescopic) closing movement, the transportation lock 29 is opened and the container 3 released in axial direction preferably during or after piercing or opening the container 3 and/or preferably during only a last part of the movement and/or just little before the final completely closed position is reached or just when the final completely closed position is reached.

During the closing movement, the transportation lock 29 is preferably opened by the direct or indirect interaction with or actuation by the housing of the nebulizer 1, the inner part 17 or its lower part 17*b* or the like. Preferably, the container 3 and/or first closure 25 are opened as well as the transportation lock 29 by means of a common actuation and/or component, here the closing movement of the nebulizer 1 or its housing or bottom part 18.

FIGS. 4 & 5 show the transportation lock 29 in the open position, i.e., wherein the container 3 is free to move axially.

In the following, a preferred embodiment of the nebulizer 1 according to the present invention will be described in more detail with reference to the further figures, wherein only essential differences from the nebulizer 1 described above or shown in FIGS. 1 to 5 will be emphasized or described. Thus, the remarks relating to FIGS. 1 to 5 apply preferably accordingly or in a similar manner, while any desired combinations of features are possible.

FIG. 6 shows the nebulizer 1 in an exploded perspective side view with in a state in which the lower housing part 18 (partly cut open for illustration purposes) with associated container 3 is separated from the upper housing part 16. The container 3 has not been inserted or pre-installed in the nebulizer 1 yet. In other words, the nebulizer 1 has not been assembled yet and is not in the preferred delivery state yet.

FIG. 7 shows the nebulizer 1 in a schematic section as well as the container 3 and lower housing part 18 which are still separated from the upper housing part 16 of the nebulizer 1.

The nebulizer 1 or its housing or housing part 18 preferably comprises a securing device 32 which may have different functions. The securing device 32 may hold the container 3 such that the container 3 is moveable back and forth within the completely closed housing for conveying the fluid 2, pressure generation and/or nebulization, wherein the securing device 32 may ensure that the container 3 is inseparable from the housing or housing part 18. Thus, only complete replacement of the housing part 18 together with the respective container 3 is possible. Alternatively or additionally, the securing device 32 may form the transportation lock 29. Alternatively or additionally, the securing device 32 may prevent that the used container 3 and/or used housing part 18 can be reconnected to or used with the nebulizer 1 once more.

When the securing device 32 or transportation lock 29 is closed, the container 3 is held for opening by inserting the conveying element or tube 9, preferably wherein a press-fit is formed between the conveying element or tube 9 and the container 3 or closure part 27, and/or for (completely) connecting the container (head) to the holder 6. In other words, the transportation lock 29 or securing device 32 form preferably a counter-bearing for the container 3 during closing of the nebulizer 1.

When the securing device 32 or transportation lock 29 is closed, the container 3 is held spaced from the piercing element 22.

Figure 6:
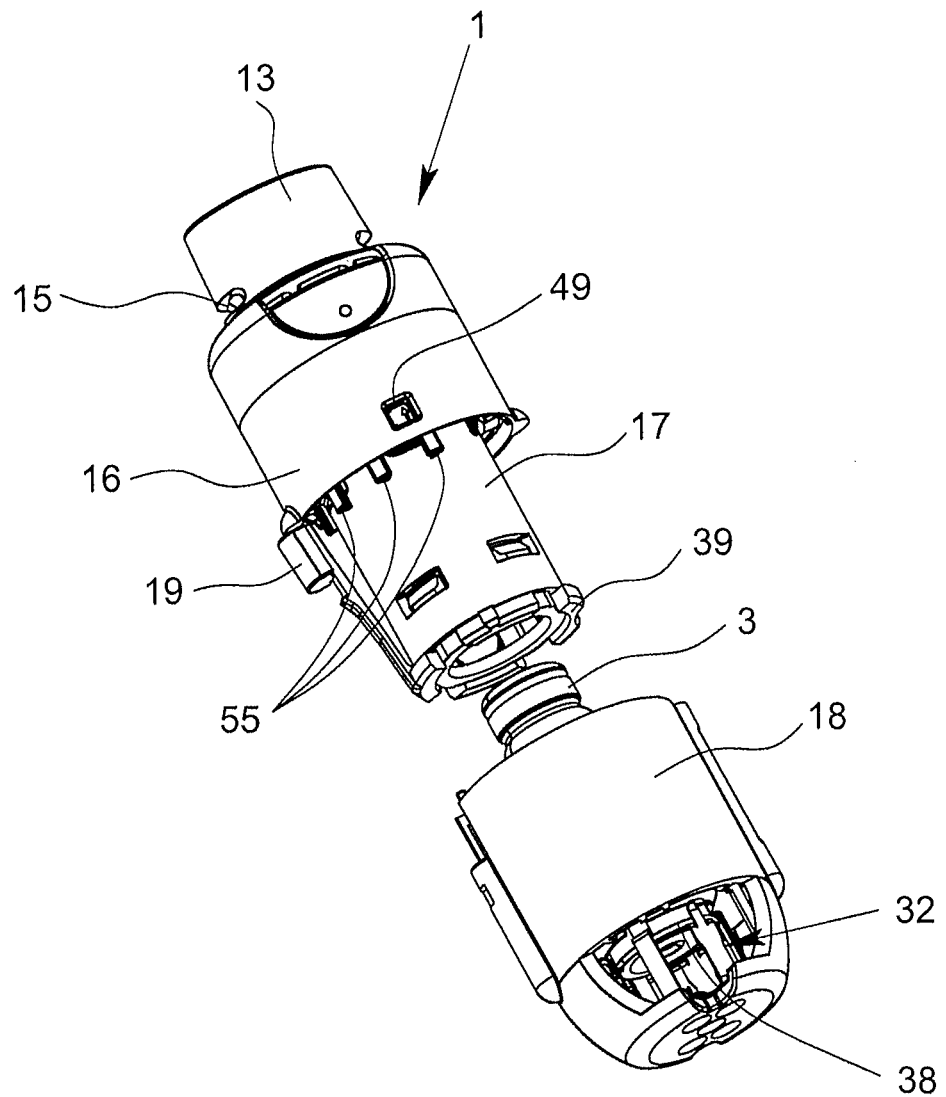
FIG. 6 is a schematic perspective view of a nebulizer according to the present invention with a separate housing part shown with a partly cut-away portion, the housing part having a securing device fixedly holding a container of the nebulizer.
Figure 7:
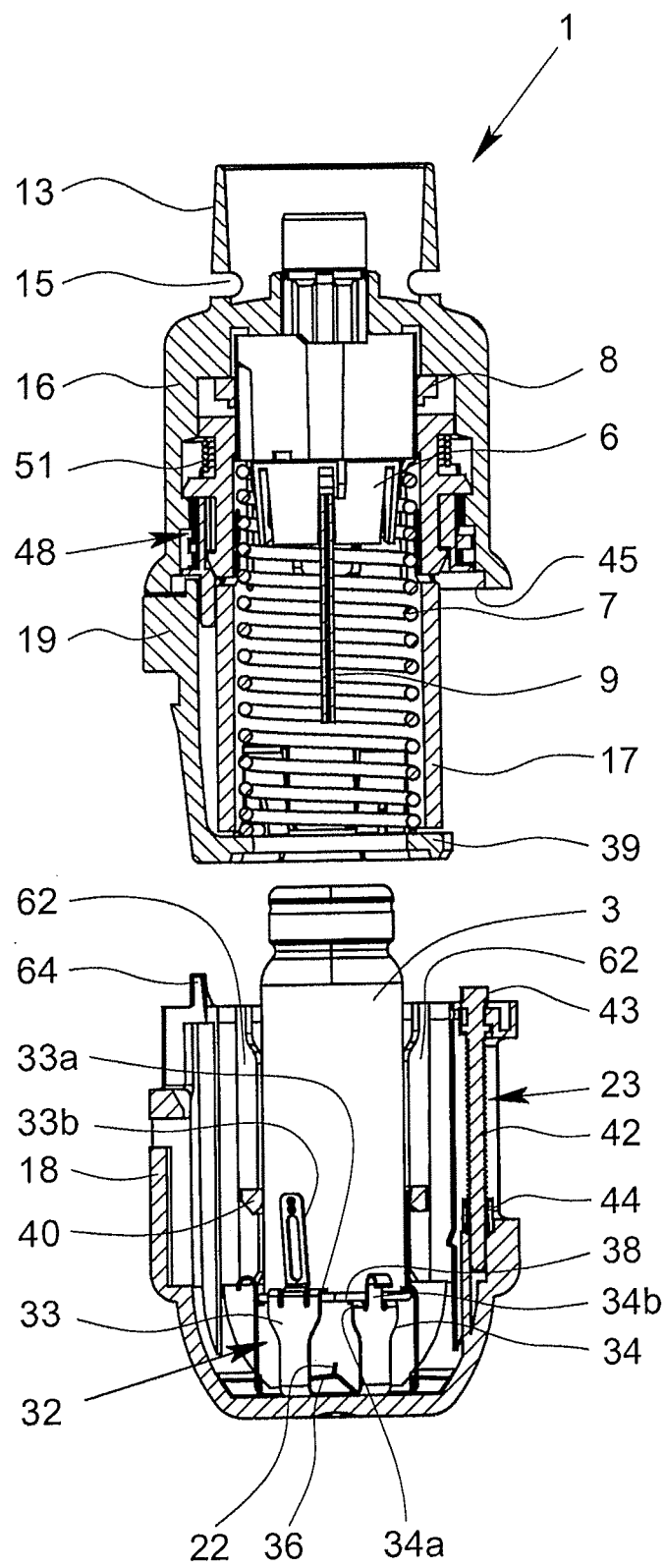
FIG. 7 is a schematic section of the nebulizer according to FIG. 6.

The securing device 32 is preferably located or arranged or fixed at or in the housing part 18 as shown in FIGS. 6 and 7.

Preferably, the securing device 32 comprises a metal and/or stamped part and/or is formed of a single, unitary part. Preferably, the securing device 32 is made of steel, in particular, spring steel. Preferably, the securing device 32 is produced from sheet material by cutting, stamping or the like and/or by bending. Preferably, the securing device 32 or a part thereof forms a cage, in particular encompassing the container 3 or an end portion thereof, in particular, the container base 21.

Preferably, the securing device 32 comprises holding elements 33 and/or locking elements 34. The elements 33 and/or 34 are preferably designed like arms, fingers, leaves or the like. In particular, the elements 33, 34 are alternately distributed over the circumference of the container 3. Preferably, the securing device 32 comprises multiple holding elements 33 and multiple locking elements 34, in particular three or more holding elements 33 and three or more locking elements 34. Preferably, the elements 33, 34 extend at least essentially axially and/or in the direction of the back and forth movement of the container 3 and/or in the direction of the longitudinal or main extension of the nebulizer 1 or main dispensing direction of the aerosol 14.

Figure 8:
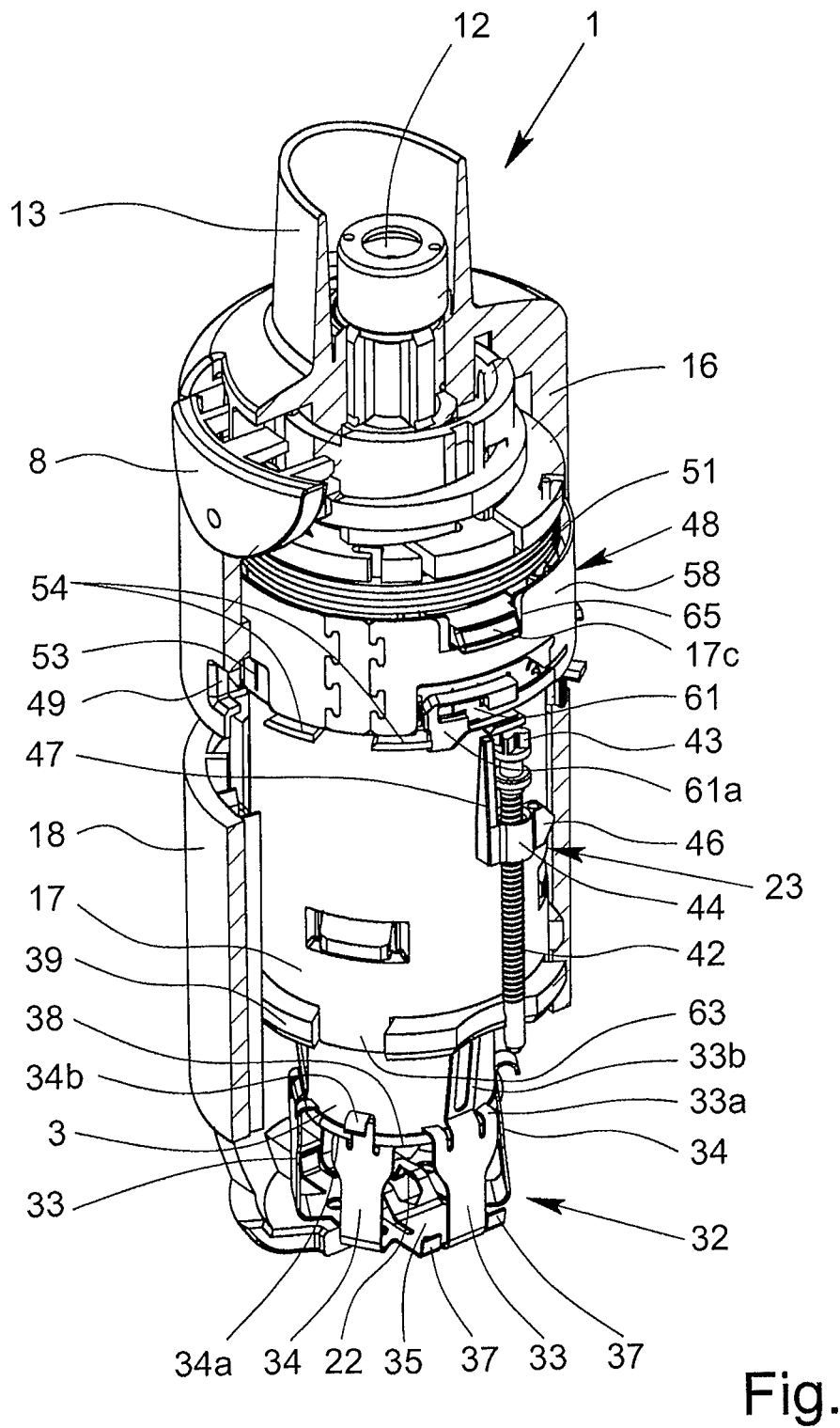
FIG. 8 is a schematic side view of the nebulizer according to FIG. 6 with partly mounted housing part and with some cut-away portions, the container being held in a fixed position.

Preferably, the elements 33, 34 are held by or connected with a base 35 of the securing device 32, as shown in FIG. 8. FIG. 8 shows the nebulizer 1 in a schematic side view with already partly mounted housing part 18 and with some cut-away portions. The transportation lock 29 or securing device 32 is still closed or locked, i.e., the container 3 is still securely held so that it cannot axially move (axially means in the direction of the back and forth or stroke movements).

Preferably, the securing device 32 or base 35 comprises or holds the piercing element 22 for piercing the container 3, i.e., opening the container base 21 or its venting hole 31 or a respective sealing of the container 3 or the like in the activated and tensioned state, i.e., when the container 3 reaches its lower end position. In the illustrated and preferred embodiment, the piercing element 22 is formed by a respective bending of a spring portion 36 of the securing device 32 or its base 35. The spring portion 36 can support or facilitate the (complete or final) connection of the container 3 to the holder 6.

The securing device 32 or base 35 preferably comprises at least one or multiple fixing portions 37 for fixing the securing device 32 at or in the nebulizer 1 or housing or housing part 18. In particular, the fixing portions 37 may fix the securing device 32 when it is pressed into the housing part 18 by cooperating with the sidewall of the housing part 18. However, it is also possible to over-mold the securing device 32, its base 35, the fixing portions 37 or the like. Moreover, the securing device 32 could be connected with the housing part 18 or the like in any other suitable manner, in particular, by a separate fixing member, by gluing or the like.

As already mentioned, the securing device 32 preferably forms the transportation lock 29 for holding the container 3 unmovable in the housing or housing part 18 in the delivery state of the nebulizer and/or before attaching the housing part 18 to the nebulizer 1. In this situation (in particular in the delivery state), the container 3 or a preferably radially protruding and/or circumferentially extending part or edge 38 thereof, preferably formed at the container base 21, is held preferably in a form-fit manner and/or between the holding elements 33 and locking elements 34, in particular between respectively formed or bent end portions 33a and 34a of the elements 33 and 34, respectively, as shown in FIGS. 6 to 8.

In the illustrated embodiment, the container 3 and/or edge 38 is caught between the end portions 33a and 34a, preferably alternatively. The holding elements 33 and/or end portions 33a grip or extend over the edge 38, and the locking elements 34 or its end portions 34a grip or extend under the edge 38, so that the edge 38 and container 3 are securely held in between, in particular by form-fit, preventing any axial movement of the container 3 relative to the securing device 32 and relative to the associated housing part 18 in this state, i.e., with locked transportation lock 29/securing device 32.

Preferably, the end portions 33a and/or 34a are formed like claws or the like and/or extend preferably radially inwardly.

Preferably, the elements 33 and/or 34 can flex with its free ends radially outwardly.

Preferably, the securing device 32 is designed such that the associated container 3 can be connected with the securing device 32 by a respective axial force or movement, wherein the elements 33 and/or 34 flex preferably automatically outwardly as required to receive the container 3 in the locked position as shown in FIGS. 6 to 8. However, if necessary, a suitable tool (not shown) or the like could be used alternatively or additionally for assembly if necessary.

For example, the ends of the end portions 33a could be inclined such that the container 3 may be inserted into or connected with the securing device 32 by a respective axial movement so that the holding elements 33 flex outwardly to allow passing of edge 38.

Preferably, the holding elements 33 or its end portions 33a prevent separation of the container 3 from the securing device 32 and, thus, from the associated housing part 18 or the like.

In the present embodiment, the holding elements 33 extend preferably above the end portions 33a and/or form or comprise preferably arm-like guiding and/or locking portions 33b. These axial extensions and/or these portions 33b extend axially beyond the end portions 33a and/or may cooperate with the container 3 or its edge 38 during axial assembly of the container 3 with the securing device 32 such that the holding elements 33 are flexed sufficiently outwardly so that the edge 38 can pass the end portions 33a and the container base 21 can be seated on the end portions 34a of the locking elements 34.

The locking elements 34 preferably comprise actuation portions 34b at its free ends extending axially beyond the end portions 34a. The actuation portions 34b may radially guide the container 3 and/or facilitate insertion of the container 3 or its edge 38 between the free ends of the locking elements 34 although the locking elements 34 are preferably radially inwardly biased as well as the holding elements 33.

When, the container 3 is held with its edge 38 between the end portions 33a, 34a, the transportation lock 29/securing device 32 is closed, i.e., the container 3 cannot move axially within the housing part 18 or nebulizer 1.

For opening the transportation lock 29 or securing device 32, the locking elements 34 and/or its end portions 34*a* are flexed preferably radially outwardly so that the container 3 can freely move axially, in particular restricted, such that the edge 38 can only move axially within the securing device 32 and/or that the axial movement is restricted (in the drawings upwardly) by the holding elements 33 or its end portions 33*b* and/or such that the container 3 cannot be separated from the securing device 32. This opening of the transportation lock 29 or securing device 32 will take place when activating the nebulizer 1, when using the nebulizer 1 for the first time and/or when completely closing the nebulizer 1. Then, the container 3 can axially move, in particular back and forth and/or with its edge 38 between the end portions 33*a* and the piercing element 22 in the present embodiment. This situation is schematically shown in the schematic section according to FIG. 9 which shows the nebulization with closed housing or housing part 18 and with opened transportation lock 29/securing device 32.

In FIG. 9, the container 3 is shown in its lower position similar to FIG. 4, in particular, wherein the container base 21 is in contact with the piercing element 32. However, the nebulizer 1 is not shown in the tensioned state, i.e., the holder 6 is not in its lower position, i.e., the holder 6 is not yet connected with the upper end or head of the container 3. Normally, the holder 6 would be connected to the container 3 in this situation with the container 3 in the lower position. In other words, usually the nebulizer 1 or drive spring 7 would be tensioned in the situation with the container 3 being in the lower position.

Preferably, the container is finally or completely or correctly connected to holder 6 when tensioning the nebulizer 1 or its drive spring 7 for the first time after completely closing the nebulizer 1. However, it is generally also possible that the nebulizer 1 is in the tensioned state, i.e., the drive spring 7 is already tensioned and the holder 6 is in the lower position, before or during (first) assembly with lower housing part 18. Consequently, the holder 6 should directly connect with the container 3, when completely closing the lower housing part 18, and the situation shown in FIG. 9 should normally not occur.

In FIG. 9, the end portions 34*a* are moved radially outwardly in order to open the transportation lock 29 or securing device 32. This is achieved preferably by flexing the locking elements 34 radially outwardly. This can be achieved in particular by acting on the actuation portions 34*b*.

Preferably, the transportation lock 29 is opened or the locking elements 34 are flexed outwardly when completely closing the nebulizer 1 or its housing part 18, in particular by cooperation with or abutment of the inner part 17, its lower part 17*b*, a retaining part 39 and/or a securing part 40. The retaining part 39 is preferably arranged at the upper housing part 16 or inner part 17. The securing part 40 is preferably arranged in the lower housing part 18.

The retaining part 39 is connected to the lower or free end of the inner part 17 or its lower part 17*b* in order to hold, bear or support an end (the lower end) of the drive spring 7. FIGS. 3 to 5 show a preferred construction of the retaining part 39. It is preferably formed as a ring and/or provided with hooks or the like for interconnection with the inner part 17. In the preferred embodiment, the retaining element 19 forms a unitary component or portion of the retaining part 39. However, other constructional solutions are possible.

In the embodiment shown in FIGS. 3 to 5, a preferably ring-like securing part 40 opens the transportation lock 29, in particular flexible arms of the transportation lock 29, to allow axial movement of the container 3. This securing part 40 keeps the transportation lock 29 or its flexible arms open when the nebulizer 1 or its housing part 18 has been completely closed. The securing part 40 is pushed axially downwards by abutment of the inner part 17 or retaining part 39 within the housing part 18 when completely closing the nebulizer 1.

In the preferred embodiment shown in FIGS. 6 to 15, and particular in FIG. 9, the nebulizer 1, housing part 18 or securing device 32 comprises the preferably ring-like securing part 40 for opening the transportation lock 29/securing device 32 or its locking elements 34. In particular, the securing part 40 is pushed axially downwards when closing the nebulizer 1 so that it is moved between the locking elements 34 or its actuation portions 34*b* and exerts an axial force radially outwards. Preferably, an inclined plane converts the axial or closing movement into an opening or radial movement which forces the actuation portions 34*b* radially outwardly when the securing part 40 is forced axially downwardly, here by abutment of the retaining part 39, in particular in the axial end position shown in FIG. 9.

Preferably, the securing part 40 and/or locking elements 34 or actuation portions 34*b* comprise a respectively inclined guiding surface 41 or the like to convert the axial closing movement or movement of the securing part 40 into the desired radial opening movement of the locking elements 34 or actuation portions 34*b* and, thus, of the end portions 34*a* to open the transportation lock 29, in particular when the housing has been completely closed or when the housing part 18 has been pushed completely on the nebulizer 1.

However, other constructional solutions are possible to realize opening of the transportation lock 29 or securing device 32 or its locking elements 34 or end portions 34*a* when closing the nebulizer 1 or its housing parts 18.

In the preferred embodiment, the securing part 40 serves alternatively or additionally another purpose. Namely, the securing part 40 prevents the locking portions 33*b* from moving radially apart or flexing radially outwards before the nebulizer 1 is assembled with its housing part 18 for the first time.

As already mentioned, the securing device 32 preferably prevents that a container 3 can be connected to or used with the nebulizer 1 once more. In particular, the securing device 32 can prevent a used housing part 18 or used container 3 from being reconnected to the nebulizer 1 once it has been detached from the nebulizer 1. Thus, the securing device 32 prevents any undesired reuse of the container 3 and/or housing part 18 with its preferably inseparable container 3.

In the present embodiment, the undesired reuse is prevented in that the locking portions 33*b* force apart or move apart or radially and/or outwards at least after the used container 3 and/or housing part 18 has been detached from the nebulizer 1 such that the used container 3 and/or housing part 18 cannot be connected to or used with the nebulizer 1 once more. Preferably, the locking portions 33*b* are biased such that the locking portions 33*b* force apart or move radially and/or outwards after release.

In the preferred embodiment, the locking portions 33*b* are held together or held against moving apart, radially and/or outwards by the securing part 40 (schematically indicated in FIG. 7) before the container 3 and the associated housing part 18 have been connected to the nebulizer 1 for the first time. In this pre-assembly state, the securing part 40 is located preferably near the free ends of the locking portions 33*b* and/or it encompasses that locking portions 33*b* such that locking portions 33*b* are held sufficiently close together to be inserted with its free ends within the retaining part 39 and/or drive spring 7 when pushing the housing part 18 axially onto the nebulizer 1 or its inner part 17, in particular lower part 17*b*.

Figure 9:
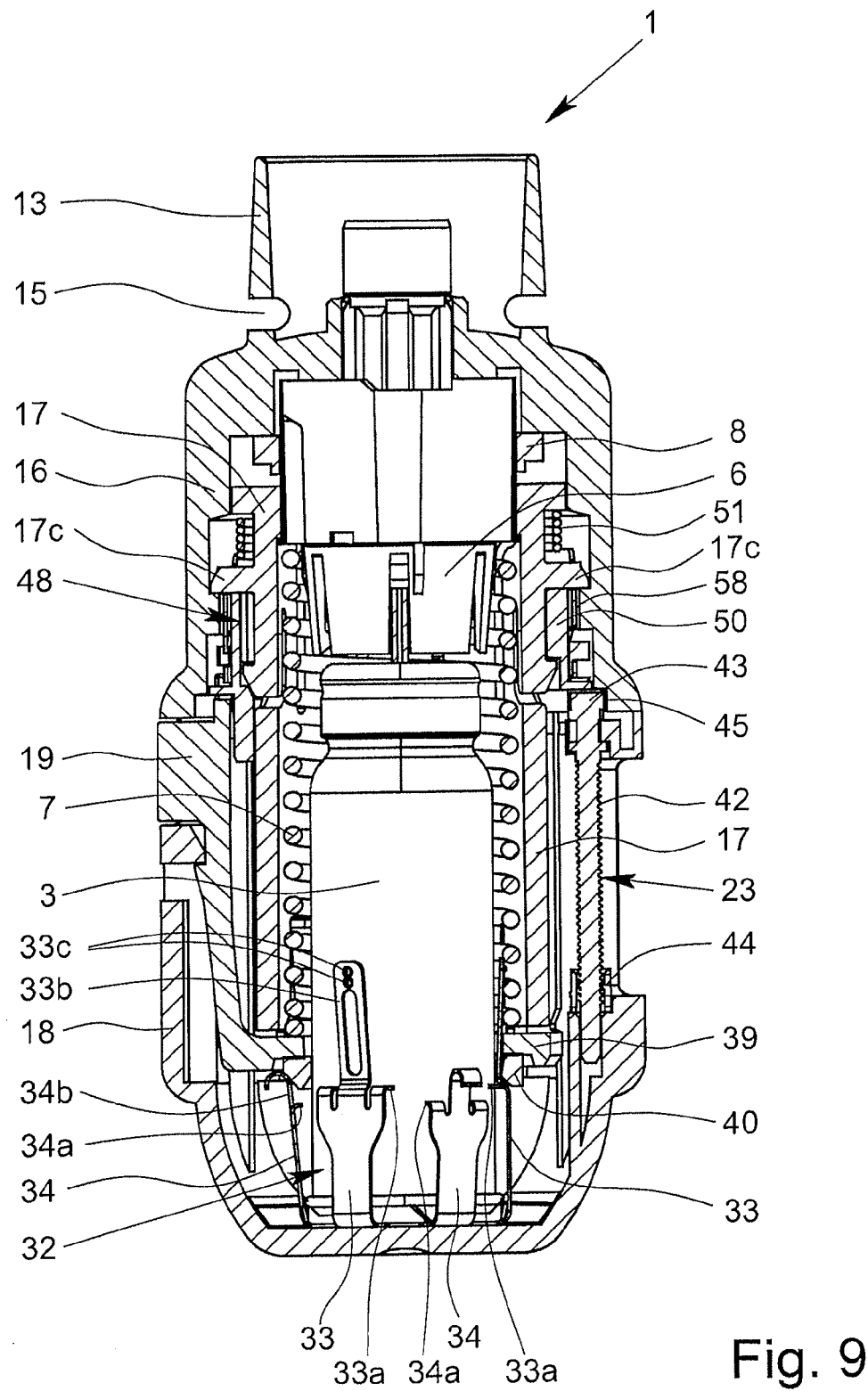
FIG. 9 is a schematic section of the nebulizer according to FIG. 6 in the completely closed state with opened securing device so that the container can move axially.

The securing part 40 may cooperate with the locking portions 33*b* or protrusions 33*c* thereof (shown in FIG. 9) preferably such that the securing part 40 is held by a preferably radial engagement and/or frictional force in its (upper) position holding the locking portions 33*b* or holding elements 33 together in the pre-assembly state. Later during assembly, in particular during complete closing of the housing or pushing on the lower housing part 18, the locking portions 33*b* are moved within the retaining part 39 and drive spring 7, while the securing part 40 is moved axially downwards or towards the securing device 32, the container base 21 and/or bottom part of the end of the lower housing part 18. Then, the end position or completely assembled position is reached as shown in FIG. 9. In this state, the radially biased locking portions 33*b* are held together by the drive spring 7 as the securing part 40 does not hold the locking portions 33*b* together any more.

Preferably, the securing part 40 has opened the transportation lock 29 or locking elements 34 in the last part of the closing movement or just when completely closing the nebulizer 1 as already mentioned.

Figure 10:
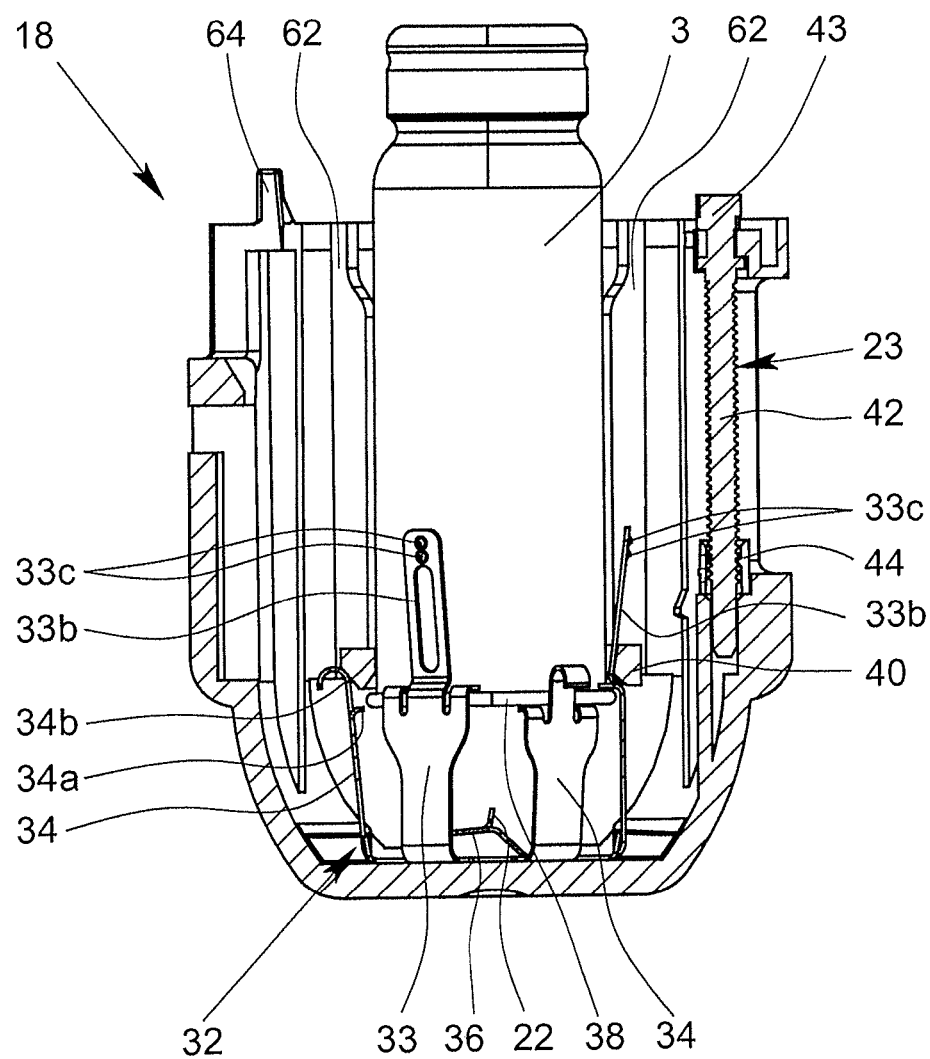
FIG. 10 is a schematic section of the housing part with the associated container after use or separation from the nebulizer.

The schematic section of FIG. 10 shows the housing part 18 together with its associated container 3 after it has been used and separated from the nebulizer 1. The securing part 40 remains preferably in its lower position. The transportation lock 29 is (still) open. The container 3 is shown in its upper position where it is held by the end portions 33*a* of the holding elements 33 when detaching the container 3 from the nebulizer 1, in particular from the holder 6 and the conveying element or tube 9.

FIG. 10 shows that the locking portions 33*b* have been forced apart, in particular due to its biasing or elastic force, here moved radially outwardly with its free ends in particular due to its preferably radial biasing or elastic force. This forced apart position of the locking portions 33*b* blocks reconnection of the container 3 and/or housing part 18 and/or securing device 32 with the nebulizer 1. Thus, the already used container 3 cannot be reused. Thus, misuse of the container 3 or nebulizer 1 can be prevented.

The securing part 40 may additionally secure the holding elements 33 or its end portions 33*a* against radial opening when the securing part 40 is in its lower position as shown in FIGS. 9 and 10. In this case, the securing part 40 contacts the holding elements 33 preferably on the outer side to prevent or restrict any outward flexing. Thus, the securing device 32 or its holding elements 33 or end portions 33*a* are secured against opening so that the container 3 or its edge 38 is securely held within the securing device 32 or the cage formed by the securing device 32 or holding elements 33.

In the preferred embodiment, the counter device 23 is arranged preferably at the housing part 18 as schematically shown in FIGS. 7 to 10. The counter device 23 counts the actuations or operations of the nebulizer 1 or the discharged doses. Preferably, the counter device 23 counts actuations or operations by detecting the rotation of the inner part 17 relative to the upper part 16 of the housing. With other words, the counter device 23 may count the tensioning the nebulizer 1 or its drive spring 7. However, other constructional solutions are possible.

Preferably, the counter device 23 comprises a threaded spindle or shaft 42 with an associated, preferably unitary formed drive gear 43. The counter device 23 preferably comprises further a rider 44 associated to the threaded shaft 42 and cooperating with the threaded shaft 42 such that the rider 44 is axially moved along the threaded shaft 42 as the shaft 42 is rotated.

The threaded shaft 42 is rotationally supported preferably in the lower housing part 18 and/or extents preferably parallel to the axial or longitudinal direction of the nebulizer 1 and/or to the axial or stroke movement of the container 3.

The drive gear 43 is located preferably at an upper end of the threaded shaft 42 and/or housing part 18, in particular such that it can mesh with a preferably inner teeth 45 of the housing or upper housing part 16 of the nebulizer 1 in the assembled state, i.e., when the housing of the nebulizer 1 is completely closed, as schematically shown in FIG. 9.

The counter device 23 or its rider 44, in particular the axial position of the rider 44 along the threaded shaft 42, may show or indicate the number of operations, in particular of tensioning, actuations or doses, which have already been performed or used with the current container 3 or which can still be performed with the current container 3. This operation number can in particularly been shown by a pointer 46 and/or an associated scale or the like which are visible reasonable through a corresponding window or transparent part of the housing part 18. It is noted that the number has not be shown precisely. In particular, it may be sufficient that the counter device 23, the rider 44 or its pointer 46 give a rough indication of the number. For this purpose, it may be sufficient if the scale shows only different coloured areas or regions roughly indicating said number. Further, it is noted that other constructional solutions are possible as well.

The counter device 23 works preferably mechanically. This allows a very simple and robust construction and a very secure operation.

The counter device 23 may control or provide preferably locking of the nebulizer 1, indicating any required container replacement and/or container counting. For this purpose, the monitoring 23 or the rider 44 preferably comprises an actuation part 47 as schematically shown in FIG. 8. The actuation part 47 is preferably ridge-like and/or extending in axial direction and/or towards the upper housing part 16 and/or upwards.

The counter device 23 is associated to the respective housing part 18 and, thus, preferably to only one container 3 and counts operations of the nebulizer 1 with the respective container 3, i.e., counts (only) the number of doses of fluid 2 removed or still removable from this container 3.

It is noted that the first container 3 may be pre-installed together with the associated housing part 18 in the delivery state. This pre-installment is optional. Preferably, further separate containers 3 are delivered together with the nebulizer 1, wherein each container 3 is inseparably connected with an associated housing part 18 and, thus, with an associated counter device 23. Preferably, the counter device 23 or threaded shaft 42 of each housing part 18 is designed or provided with inhibition or brake means, such that any undesired counting or rotation is prevented before the respective housing part 18 is mounted to the nebulizer 1.

The nebulizer 1 preferably comprises a device 48 for counting the number of containers 3 that have been used or still can be used with the nebulizer 1 and/or for indicating or displaying said container numbers and/or symbols indicating container replacement and/or end of use. This device 48 is preferably for monitoring and/or user guidance.

Preferably, said numbers and/or symbols are visible or shown through a transparent part or window 49 of the nebulizer 1, in particular located in the upper housing part 16 as schematically indicated in FIG. 6. In particular, said numbers and/or symbols are shown at a side face of the nebulizer 1. Other arrangements or constructional solutions are possible.

Figure 11:
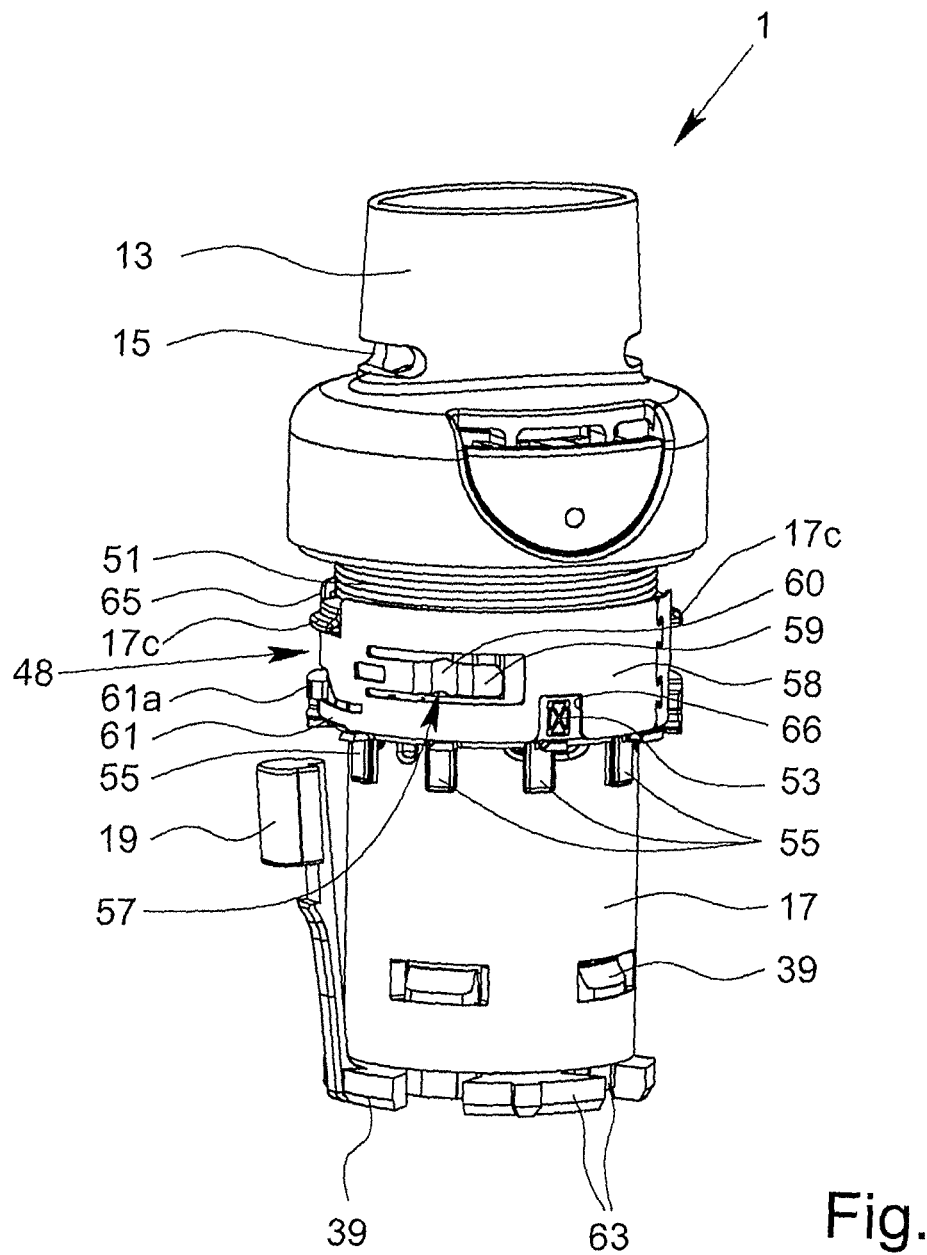
FIG. 11 is a perspective view of an upper part of the nebulizer according to FIG. 6 without the housing part and with partly cut-away portions.

FIG. 11 shows the nebulizer 1 without lower housing part 18 and without container 3 in a schematic side view, wherein parts of the upper housing part 16 have been cut-away so that the monitoring or guidance device 48 of the nebulizer 1 is better visible.

The nebulizer 1 or device 48 preferably comprises a member 50 for indicating or displaying said container number, symbols, a status, and/or user instructions, e.g., relating to container replacement, and/or for controlling locking of the nebulizer 1. Thus, the member 50 is also called indicator member and/or control member. Preferably, both functions are achieved by the same or one single member 50. However, it is also possible that the indicator member and the control member are formed by separate parts or multiple parts. Preferably, the following description shall be understood in such a broad sense.

Preferably, the nebulizer 1 or device 48 comprises a spring 51 for driving or moving, in particular rotating, the member 50. This spring 51 is shown in FIGS. 7, 8, 9 and 11. Preferably, the member 50 is driven or rotated—in particular in multiple steps and/or from an initial (rotational) position to a final (rotational) position—only by spring force or by means of the spring 51.

The spring 51 is preferably a helical, sleeve-like, ring-like and/or torsional spring and/or a leg spring. It is preferably located coaxially with and/or adjacent to the driven member 50.

The spring 51 is preferably mounted in a biased state so that it applies a rotational force to the member 50. For this purpose, the spring 51 is supported with one end or leg at the nebulizer 1, in particular at the upper housing part 16, and engages with its other end or leg with member 50, e.g., by abutting a respective shoulder or bearing portion 67 (shown in FIGS. 12 and 13) of the member 50 or the like.

FIG. 12 shows a preferred embodiment of the member 50 in a schematic side view. FIG. 13 shows the member 50 in a perspective view.

The member 50 is preferably formed by a unitary and/or molded part. The member 50 is preferably at least essentially ring-like and forms or comprises a preferably closed ring.

The member 50 comprises or is provided with numbers 52 indicating said container number, and/or with said symbols 53 for user guidance, in particular for indicating container replacement and/or end of use of the nebulizer 1. Preferably, the numbers 52 and symbols 53 are shown and/or arranged on the member 50 such that one or more numbers 52 and one or more symbols 53 alternate. In particular, between preferably consecutive numbers 52 one or more symbols 53 are arranged and/or shown such that these symbols 53 indicate e.g., necessary container replacement, opening of the nebulizer 1, closing of the nebulizer 1 or the like. This may be communicated or indicated by respective arrows, colours, marks or the like as symbols 53. Further, the last symbol 53 may indicate end of use of the nebulizer 1 or complete locking of the nebulizer 1, e.g., by an "X" or the like. This symbol 53 may be shown for example when the allowable number of operations or actuations of the nebulizer 1 have been reached or exceeded of the last container 3 that may be used with or in the nebulizer 1, i.e., indicating total or final locking of the nebulizer 1. In the present embodiment, preferably a sequence of at least two different symbols 53 is shown between different or consecutive numbers 52. This sequence of symbols 53 preferably comprises a first symbol 53 (e.g., arrow downwards) indicating opening of the nebulizer 1 for container replacement and a second symbol 53 (e.g., arrow upwards) indicating closure of the nebulizer 1 for completing container replacement. However, it is also possible to show only one, potentially similar or identical symbol 53 between the different or consecutive numbers 52, such as one symbol 53 indicating container replacement. Preferably, only one special or end symbol 53, such as "X", is shown at the end when the allowable number of operations or actuations of the nebulizer 1 has been reached or exceeded for the last container 3 and/or when the nebulizer 1 is finally blocked and/or when no further container 3 can be inserted.

The member 50 preferably comprises engagement or stop portions 54 which are preferably formed by radial protrusions or the like in the present embodiment. The stop positions 54 are used preferably to allow or realize a stepwise movement or rotation (indexing) of the member 50.

The member 50 comprises further preferably blocking portions 55 which extend preferably axially and/or cooperate with the retaining element 19 to selectively lock the nebulizer 1 or housing part 18 against opening, in particular by selectively blocking the retaining element 19 against depressing or radial inward movement.

The member 50 preferably comprises control portions 56 for controlling or driving an associated lock 57 of the nebulizer 1. The control portions 56 are formed preferably by protrusions or indentions or inclined guiding surfaces or the like which preferably extend radially and/or which are preferably formed on an outer circumference of the member 50 or its ring portion. However, other arrangements are possible as well.

The lock 57 is preferably formed by a locking member 58 or a portion 59 thereof, which is preferably tongue-like, leaf-like and/or flexible. FIG. 14 shows in a perspective view the locking member 58. FIG. 15 shows in other perspective view the locking member 58.

The locking member 58 is preferably made of metal and/or formed by plate material and/or a stamped part or the like. The locking member 58 is preferably ring-like and/or sleeve-like.

The portion 59 is preferably bent or indented or provided with such a form, in particular in radial direction and/or provided with a crimp, corrugation 60 or the like, for cooperating with the member 50 and/or at least one or more or all of the control portions 56, in particular such that depending on the rotational movement or position of the member 50 the portion 59 is radially flexed, in particular outwards, or not. For example, the control portions 56 are indented or recessed so that a portion 59 is not flexed radially outwards if the respective corrugation 60, which extends radially inwards from the respective portion 59, is received in a portion 56 located adjacent to this corrugation 60 on the inner side. If the member 50 is in another rotational portion, the corrugation 60 may abut on the non-recessed outer periphery of member 50 so that the respective portion 59 is flexed outwards and the lock 57 is closed. Thus, the lock 57 is driven or controlled, namely closed and opened, by means of the control member 50, in particular depending on its rotational position.

As already mentioned, the device 48 or member 50 is preferably driven by spring force, in the present embodiment by the force of spring 51. In particular, the member 50 is rotated or indexed stepwise by means of the force of the spring 51, wherein a ratchet or stop mechanism is provided to ensure the only stepwise moving or rotating of the member 50. In particular, stop means engage with the stop portions 54 of the member 50. In the present embodiment, the mechanism or stop means are preferably formed by one or two stop elements 61. The stop elements 61 are preferably formed like arms and/or by the locking member 58. The stop elements 61 are preferably elastically flexible to selectively allow a stop portion 54 to pass, i.e., to selectively allow the member 50 to index one step further, or to block a stop portion 54 and, thus, member 50 against further rotation. Preferably, the stop elements 61 are biased into a stopping position such that each stop element 61 extends into the way of movement of the stop portions 24 such that no stop portion 54 can pass the respective stop element 61.

Preferably, at least two stop elements 61 are provided and preferably offset such that stop elements 61 can be actuated alternatively to allow the member 50 to index or move further by one step, i.e., by one rotational movement or increment when the stop elements 61 are alternatively actuated, e.g., flexed, in particular in axial and/or radial direction, to allow one stop portion 54 to pass. The stop elements 61 are preferably flexed upwards to allow the respective stop portion 54 to pass. The actuation of the stop elements 61 will be explained in more detail below.

The stop elements 61 or its free ends may be provided with a broadened abutment or engagement body or surface, in particular by respectively bending the element or arm 61, by overmolding or the like. Each stop element 61 may be provided with a contact element 61a as schematically shown in FIG. 8. The contact element 61a may be formed by overmolding and/or may be schoe-like. The contact element 61a may form a stop or abutment for the stop portions 54 such that the member 50 is blocked against further rotation by force of spring 51 when the stop element 61 or contact element 61a is in the blocking position, here in the lower position shown in FIG. 8 where one stop portion 54 abuts the contact element 61a and can not pass in circumferential direction. Here, the stop element 61 or contact element 61a is moved upwards or axially so that the blocked stop portion 51 can pass and the member 50 can index one step further in circumferential direction.

In the following, the operation and handling of the nebulizer 1 will be explained in more detail.

The nebulizer 1 may be delivered with a pre-installed container 3 and pre-attached housing part 18. In this case, the nebulizer 1 or its housing part 18 is not completely closed so that the container 3 is not yet fluidically connected or opened.

Alternatively the nebulizer 1 may be delivered with a separate container 3 and housing part 18. In this case the container 3 and the housing part 18 are preferably pre-assembled, i.e., form a unit that is separate from the nebulizer 1.

In any case, the nebulizer 1 is preferably delivered together with multiple containers 3, e.g., four or five containers 3, wherein each container 3 is inseparably connected to an associated housing part 18. These units of containers 3 and housing parts 18 can be exchanged so that the nebulizer 1 can be used with multiple containers 3 one after the other.

In both cases, the container 3 is preferably held unmoveably at or within the housing part 18 by the closed transportation lock 29 or securing device 39.

In both cases, the housing part 18 preferably comprises a coding, e.g., by one or more grooves, protrusions, ribs 62 or the like distributed around the inner circumference of the housing part 18 and/or axially extending, as schematically indicated in FIG. 10. This coding corresponds to the container 3 or the respective fluid 2 associated to the housing part 18. The coding matches to a complementary coding at the nebulizer 1, in particular at the inner part 17 or retaining part 39, and is preferably formed by respectively arranged and/or dimensioned indentions, coding portions 63, such as protrusion, indentions, recesses or the like, in particular formed by or at the retaining ring or part 39, as schematically shown in FIG. 11. Only when the codings match, the housing part 18 and, thus, the container 3 can be pre-installed and/or (completely) connected to or with the nebulizer 1.

Before (completely) closing the nebulizer 1 or its housing part 18, the device 48 or indicator member 50 may indicate by a respective symbol 53, such as an arrow pointing upwards, to completely close the nebulizer 1 or housing part 18.

When the housing part 18 is completely closed, the container 3 associated to the housing part 18 is fluidically connected to the nebulizer 1. This is detected or registered by the nebulizer 1 or device 48. This detection of the connection of the housing part 18 and, thus, of an associated container 3 is preferably realized mechanically, in particular by actuating one of the stop elements 61 to allow the member 50 to index one step further, i.e., until the other stop element 61 stops further indexing or rotation of the member 50. In the present embodiment, this registration or actuation is preferably achieved by a protrusion 64 formed at the housing part 18, in particular at its upper front face, as shown in particular in FIG. 7. When completely closing nebulizer 1, the protrusion 64 abuts one associated stop element 61 or contact element 61a and consequently flexes the stop element 61 or contact element 61a upwards such that it does not stop a corresponding stop portion 54 of the member 50 any more, but allows the member 50 to move or rotate one step further, i.e., until the other stop element 61, which has not been flexed out of engagement in this state, stops further rotation by stopping a corresponding stop portion 54, preferably another one of stop portions 54.

As already mentioned, the container 3 is preferably inseparable from the housing part 18, the associated counter device 23 and/or associated securing device 32. Thus, after connection of a new container 3 with the nebulizer 1, the associated counter device 23 starts counting of the number of operations or uses of the respective container 3 that have already been performed or still can be performed. This operation number may be indicated or shown by the counter device 23 or its rider 44 or pointer 46 as already mentioned, while the device 48 or member 50 preferably only shows the container number 52, i.e., the number of containers 3 that have already been used or still can be used with the nebulizer 1.

Preferably, the nebulizer 1 is blocked against opening until the current container 3 has been (sufficiently) emptied, and/or until a predetermined number of operations or actuations has been reached or exceeded. This blocking of the nebulizer 1 or its housing part 18 against opening and/or container replacement is preferably achieved by a respective blocking portion 55 of the member 50 located below the retaining element 19 in this state as schematically indicated e.g., in FIG. 9, such that the retaining element 19 cannot be depressed, i.e., the nebulizer 1 cannot be opened and the housing part 18 cannot be detached.

When a predetermined number of operations or actuations of the nebulizer 1 has been reached, the nebulizer 1 is blocked against further use with the current container 3. This blocking is also called first locked state.

The first locked state is entered preferably by means of the counter device 23. In particular, the rider 44 or its actuation part 47 cooperate with the device 48 to enter the first locked state, when a predetermined number of operations have been reached or exceeded with the current container 3. Particularly, the rider 44 or its actuation part 47 reach an upper axial position in this state and actuate a respective stop element 61 or contact element 61a that is in blocking position or engagement with a stop portion 54. Thus, the stop element 61 or contact element 61a is preferably flexed or deformed such that the previously stopped stop portion 54 can pass and the member 50 is free to index one step further by the force of spring 51. FIG. 8 shows a situation, in which the rider 44 and actuation part 47 are already near the upper position and near the position to actuate the associated stop element 61 or contact element 61a. However, in the state shown in FIG. 8 one stop portion 54 and the member 50 are still blocked against rotating one step further.

The above indexing of the member 50 by one step leads to the first locked state. In this state, the nebulizer 1 or retaining element 19 is unblocked so that it can be opened. In particular, the blocking portion 55 blocking actuation of the retaining element 19 in the previous state is moved further, so that the retaining element 19 is not blocked any more, but can be actuated or pushed in order to allow detachment of the housing part 18 for container replacement.

In the first locked state, the nebulizer 1, device 48 or member 50 indicates preferably by a respective symbol 53, in particular by an arrow pointing downwards, that container replacement is necessary and/or that the nebulizer 1 is locked against further use with the current container 3.

By the above indexing of the member 50 to reach the first locked state, the nebulizer 1 is locked against further use. This is achieved in particular in that the member 50 drives the lock 57 to lock the nebulizer 1 against further actuation, preferably against further tensioning of the drive spring 7 and/or against rotating of the housing part 18. This is preferably realized in that the rotation of the member 50 flexes the lock 57 or portion 59 of the locking member 58 radially outwards so that the flexed portion 59 leaves its non-locking position, into which it is biased, and locks further rotation of the inner part 17 relative to the upper housing part 16. This locking is in particularly achieved in that a free end of the portion 59 engages into respective teeth or against respective abutment surfaces formed at the inner surface of the upper housing part 16. In this respect it is noted that the device 48 is preferably arranged or mounted on inner part 17, particular on its upper part 17a, wherein the preferably ring-like locking member 58 is preferably arranged around the rotatable member 50. The locking member 58 is preferably secured against rotation relative to the inner part 17 by respective form fit engagement, preferably of the inner part 17 or at least one protrusion 17c thereof into a recess 65 of the locking member 58. In the present embodiment, the recess 65 is preferably formed like a pocket or a portion cut-out of the periphery from one axial side. In particular, the locking member 58 may be provided with two or more recesses 65 as schematically shown in FIGS. 14 and 15, for engagement of respective protrusions 17c or the like, in particular of the associated inner part 17. However, other constructional solutions are possible as well.

Consequently, only member 50 is rotatable relative to inner part 17 and, thus, to locking member 58. However, locking member 58 is rotatable together with inner part 17 relative to upper housing part 16.

As already mentioned, the control member 50 is moveable, in particular rotatable, relative to locking member 58. This relative rotation is meant when any rotation or indexing of the control member 50 is mentioned. In this context, it is considered that the device 48 and the locking member 58 are rotated together with the inner part 17, but this rotation is different as this is the movement for tensioning the energy store, here spring 7, and/or for delivering or sucking fluid 2 out of the container 3 by in particular axial movement of the conveying element or tube 9.

The construction mentioned above, results in that the device 48 is rotated together with the inner part 17 each time the lower housing part 18 is rotated, i.e., when tensioning the drive spring 7. This rotation is preferably performed in 180° steps. Therefore, the device 48 or indicator member 50 preferably comprises two sets of respective number 52 and/or symbols 53 that are shown alternately through the window 49.

Thus, the member 50 preferably comprises two groups of numbers 52 and/or symbols 53, each group with the respective sequence of numbers 52 and/or symbols 53, wherein the groups are arranged offset by 180° on the member 50. This offset correspondence to the rotational angle for each rotational actuation of the lower housing part 18 and inner part 17 for tensioning the nebulizer 1/drive spring 7.

Preferably, the control portions 56 and/or the peripheral parts of the control member 50 in between the portion 56 form an inclined or control plane or surface cooperating with the portion 59 or its cam or corrugation 60 such that the lock 57 or the locking can be actuated alone by the force of the spring 51 acting on the member 50. In particular, the spring 51 or member 50 drives the lock 57. Further, the member 50 controls the lock 57 or the locking. As the member 50 also forms an indicator member, the indicator member drives the lock 57 or locking as well.

In the present embodiment, the locking member 58 is preferably arranged outside or around the control member 50 at least around a cylindrical main part of control member 50. In particular, the locking member 58 encompasses or covers at least substantially the cylindrical main part of the control member 50. The locking member 58 preferably comprises two openings 66 (shown in FIGS. 14 and 15) that are alternately aligned with window 49 depending on the rotational position of inner part 17 and, thus, of the locking member 58 so that the respective number 52 and/or symbol 53 is visible through the window 49 and through locking member 58.

In the first locked state, the member 50 is preferably stopped against further rotation by the protrusion 64 where any other part corresponding to the attachment of the housing part 18. When the housing part 18 is detached from the nebulizer 1 or its upper housing part 16 or inner part 17 for container replacement, this detachment is registered by unblocking the further movement or rotation of the member 50. In particular, a stop portion 54 of the member 50 which has been stopped by protrusion 64 or the like, can pass after detachment of the housing part 18 so that the member 50 can index one step further. In this further rotational position, the nebulizer 1 is still in its first locked state, i.e., is still locked against further use, in particular against further actuation or tensioning of the drive spring 7. However, the member 50 may show the next symbol 53, in particular an arrow pointing upwards, indicating that a new container 3 is connected and/ or that a new housing part 18 is connected to the nebulizer 1. This situation correspondents to the initial situation before first assembly of the nebulizer 1 with the housing part 18 as already described.

It is noted that the blocking element 8 is preferably blocked against actuation, in particular against release of the holder 6 and drive spring 7 in the first locked state. This actuation locking will also be achieved by the device 48 or member 50.

When the housing part 18 and the associated container 3 have been replaced, this is registered by the device 48, in particular by actuation of the corresponding stop element 61 by means of the protrusion 64. Then the member 50 indexes one step further and shows the next container number 52. Then, the lock 57 is reset, i.e., opened or unlocked again. Thus, the nebulizer 1 is unlocked and can be used further with the new container 3. Simultaneously, the container 3 or housing part 18 is preferably locked again against opening or container replacement, in particular in that the next blocking portion 55 is positioned below retaining element 19 to prevent actuation of the retaining element 19 which is necessary for opening the nebulizer 1.

The above sequence can be repeated, i.e., new containers 3 and new housing parts 18 can be used one after the after with the nebulizer 1, wherein the device 48 or indicator member 50 displays or shows the container number 52 and, preferably, symbols 53 for user guidance, in particular to indicate any necessary container replacement and/or indicating to open and close the nebulizer 1 or the like. The container number 52 relates in particular to the number of containers 3 that have already been used with the nebulizer 1 or still can be used with the nebulizer 1. In particular, one or more symbols 53 are displayed or shown alternately with the consecutive container numbers 52. This is realized preferably by a common component, namely indicator member 50. However, other constructional realizations are possible.

Further, the display of the container numbers 52 and/or symbols 53 works preferably only mechanically. In particular, the device 48 and/or the lock 57 work only mechanically.

After a predetermined number of containers 3 have been connected to or with the nebulizer 1, the nebulizer 1 will be blocked against further container replacement. After using the lastly inserted or connected container 3, the nebulizer 1 will enter the final locked state, i.e., the second locked state, preferably where the lock 57 or nebulizer 1 is blocked against resetting and/or the nebulizer 1 or housing part 18 is blocked against opening. This second locked state is entered in particular after the predetermined number of operations has been reached or exceeded with the ultimate, current container 3. Similar to the previous process the counter device 23 or its rider 44 or actuation part 47 actuates the device 48, in particular the corresponding stop element 61 to allow to index the member 50 one step further into its final rotational position. Thus, the second locked state is entered.

In the second lock state, the control member 50 cannot be rotated any further. This is realized in the present embodiment in particular in that the bearing portion 67 abuts one protrusion 17*c* of the inner part 17 engaging into one of the recesses 65. However, other constructional solutions are possible in order to realize the desired rotational stop or blocking for the control member 50 in the final rotational position, i.e., in the second locked state.

In the second locked state, the device 48 or member 50 does not allow opening of the nebulizer 1 or housing part 18 as it would be in the case in the first locked state. Instead, the member 50 comprises a respectively designed, preferably sufficiently long blocking portion 55 to block the retaining element 19 further against actuation and, thus, to block the nebulizer 1 against opening and container replacement.

In the second locked state, the nebulizer 1 can be locked against further actuation, in particular against tensioning of the drive spring 1 and/or rotation of the housing part 18 or inner part 17. This can be realized by actuating the lock 57, in particular by flexing portion 59 radially (preferably outwards) by the member 50 or its corresponding control portion 56. In the second locked state, the nebulizer 1 is preferably locked against any further discharge of fluid 2, in particular by blocking actuation of the blocking element 8. This is preferably also realized by device 48.

Therefore, the nebulizer 1 cannot be used anymore after the second locked state has been entered. The second locked state is not reversible. In particular, resetting or unlocking of the lock 57 is not possible, but prevented in the second locked state.

As already outlined above, some general aspects or ideas of the nebulizer 1 according to the preferred embodiment can be summarized as indicated in the following.

The device 48 preferably comprises only two parts (control member 50 and locking member 58) or three parts (control member 50, spring 51 and locking member 58), but provides multiple functions, in particular displaying of numbers 42 and/or symbols 53 and/or user instructions, locking of the nebulizer 1 against further use, locking of the nebulizer 1 against tensioning, and/or locking of the nebulizer 1 against opening or container replacement.

The nebulizer 1 may comprise the indicator member 50 for showing numbers, in particular container numbers 52 and alternately symbols 53 indicating container replacement and/or nebulizer opening and/or closing. The indicator member 50 may be moved or rotated stepwise by the force of the spring 51.

The indicator member 50 may drive the lock 57 of the nebulizer 1 such that the nebulizer 1 is locked against further use in the first locked state, when he container 3 is replaced, wherein the first locked state is reset by indexing the indicator member 50 and/or resetting the lock 57 if the container 3 and/or housing part 18 have been replaced.

The indicator member 50 is preferably ring-like.

The indicator member 50 works or shows the numbers 52 and/or symbols 53 mechanically.

The nebulizer 1 preferably comprises the lock 57 for locking the nebulizer 1 against further use in the first locked state, in particular when the container 3 is replaced.

Preferably, the first locked state is reset by resetting the lock 57, if the container 3 and/or housing part 18 have been replaced. With other words, the lock 57 is preferably resettable and can be used further after container replacement. In particular, an exchange or replacement of the lock 57 is not necessary to reuse the nebulizer 1.

The nebulizer 1 preferably comprises the control member 50 for controlling or driving the lock 57.

The control member 50 is preferably moved or rotated stepwise by the force of the spring 51.

The lock 57 and/or first locked state is preferably blocked against resetting in the second locked state.

The second locked state is preferably entered when a predetermined number of containers 3 has been used or inserted into the nebulizer 1 and, preferably after a predetermined number of operations has been performed or exceeded with the nebulizer 1 after inserting the last container 3.

The control member 50 is preferably ring-shaped.

Preferably, the control member 50 forms the indicator member or vice versa.

The control member 50 preferably displays the numbers 52 of containers 3 that have been used or still can be used and/or the symbols 53 indicating containing replacement and/or user guidance or nebulizer handling.

The control member 50 blocks preferably opening of the nebulizer 1 and/or container replacement until a predetermined number of operations has been reached or exceeded with the current container 3.

Preferably, the nebulizer 1 is locked against opening or container replacement, in particular by means of the control member 50, in the second locked state.

Preferably, the nebulizer 1 is locked against opening or container replacement, in particular by means of the control member 50, before the first locked state has been reached.

Preferably, the lock 57 locks the nebulizer 1 in the first and/or second locked state against conveying fluid 2 into the pressure generator 5 and/or against tensioning of the drive spring 7 of the nebulizer 1 and/or against rotation or turning of the housing part 18 or inner part 17.

Preferably, the housing part 18 is replaced each time the container 3 is replaced. In particular, the container 3 is inseparable from the housing part 18 and/or counter device 23 or vice versa.

The moved apart locking portions 33b of the securing device 32 preferably prevent the used and/or detached container 3 from being re-connected to or reused with the nebulizer 1 once more and/or prevent a used or detached housing part 18 from being reconnected to the nebulizer 1 once more.

Preferably, the housing part 18 can be or is detached or opened for replacing the container 3.

Preferably, the securing device 32 is associated to the container 3 preventing a used container 3 from being connected or used with the nebulizer once more.

Figure 16:
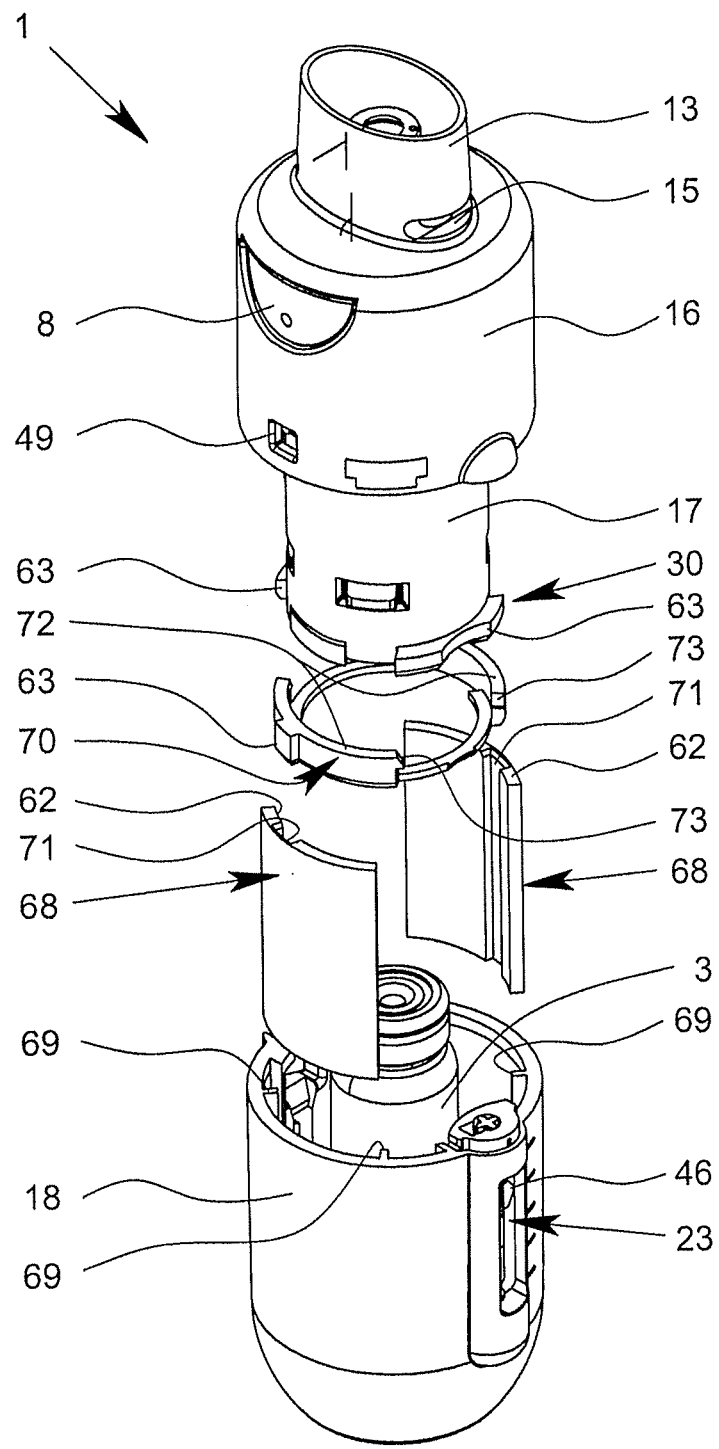
FIG. 16 is a schematic exploded view of the nebulizer according to a modified embodiment.

FIG. 16 shows in a schematic exploded view a modified embodiment of the nebulizer 1 with a preferred coding of the housing part 18 and of the nebulizer 1, in particular of the upper part 16 or inner part 17, preferably by the retaining part 39, as already been mentioned above. The modified embodiment deals with a preferred realization of the coding.

In the modified embodiment, the coding of the housing part 18 and, thus, of the container 3 and/or fluid 2, is realized by at least one insert or coding element 68, in the present embodiment by two or multiple inserts or coding elements 68, which are mounted or fixed at or in the housing part 18.

In the following, a preferred realization and/or mounting of one or multiple or all coding elements 68 is discussed.

Preferably, the coding element(s) 68 can be clipped into the housing part 18. However, other constructional solutions are possible for fixing the coding element(s) 68 at or in the housing part 18.

In the present embodiment, the housing part 18 preferably comprises radial shoulders 69 for receiving or holding the coding elements 68. In particular, the radial shoulders 69 are rib-like. Preferably, the coding element 68 can be received between two spaced shoulders 69. In particular, the coding element 68 can be pushed axially into the housing part 18.

Preferably, the coding element 68 can be arranged at the inner side of the peripheral wall of the housing part 18. Preferably, the coding element 68 is essentially plate-like and/or curved for arrangement within the preferably essentially sleeve-like portion of the housing part 18.

The coding of the housing part 18 is provided or formed by the one or more coding elements 68. This coding is associated to the container 3 which is preferably inseparably connected to or with the housing part 18.

Further, the nebulizer 1 is also provided with a coding. This coding may be formed by the inner part 17, the retaining part 39, the coding portion(s) 63 and/or a key element 70. Preferably, the key element 70 is ring-like and/or provided with one or more or all coding portion(s) 63. Preferably, the key element 70, which is shown in FIG. 16, forms part of the nebulizer 1 and/or is in particular inseparably mounted or fixable to the nebulizer 1. Preferably, the key element 70 can be attached to the inner part 17 and/or to the retaining part 39. Preferably, the key element 70 can be attached to the nebulizer 1 or inner part 17 or retaining part 39 by clipping and/or in any other suitable manner.

In particular, the key element 70 allows easy coding of the nebulizer 1.

Preferably, the key element 70 is inseparable from the nebulizer 1.

Preferably, the nebulizer 1 is coded by the peripheral location and/or extension and/or radial extension or dimension, inner or outer contour or the like of the coding portion(s) 63.

It is noted that the retaining element 39 and/or the key element 70 can be provided with the coding portion(s) 63.

In the illustrated embodiment, the key element 70 can be clipped or attached to the retaining part 39. For this purpose, the key element 70 preferably comprises at least one or two holding portions 72 which can be axially shifted onto the inner part 17 and/or over the retaining part 39 and/or between radial protrusions, coding portions 63 or the like of the retaining element 39. In the preferred embodiment, the holding portions 72 are extending essentially in a circumferential direction and/or are relatively rigid and/or support one or more coding portions 63. Preferably, the key element 70 and/or holding portions 72 are provided with shoulders or noses 73, preferably extending in circumferential direction and/or located at the circumferential ends of the holding portions 72, in order to allow fixing or clipping of the key element 70 or holding portions 72 to the nebulizer 1 or inner part 17 or retaining element 39 and/or in between radial protrusions, holding portions 63 or the like of the nebulizer 1, inner part 17 and/or retaining part 39. However, other constructional solutions are possible.

The coding provided by the one or more coding elements 68, in particular by protrusions and/or ribs 62 and/or indentions and/or grooves 71 of the coding element(s) 68 or the like, is preferably coded by the peripheral location and/or extension and/or radial extension or dimension, inner contour or the like and/or is preferably complementary to the coding provided at the nebulizer 1, in particular provided by the retaining part 39, the key element 70 and/or the coding portion(s) 63, in particular respective protrusions, recesses or the like.

Only if the codings of the nebulizer 1, on one hand, and the housing part 18, on the hand, match can the nebulizer 1 be closed, in particular, by shifting the housing part 18 on the inner part 17. If the codings do not match, the respective housing part 18 and the associated container 3 cannot be used with the respective nebulizer 1.

The possibility to code the nebulizer 1 and/or housing part 18 by means of additional parts, such as the coding elements 68 and/or key element 70, in particular by attaching or clipping respective parts to the nebulizer 1 and/or housing part 18, allows in particular a medicament or fluid specific coding in an easy manner and/or allows a specific coding later after producing multiple nebulizers 1 and/or housing parts 18, in particular independently from production and/or depending on demand.

As already mentioned, individual features, aspects and/or principles of the embodiments described may also be combined with one another as desired and may be used particularly in the nebulizer according to FIGS. 1 & 5 but also in similar or different nebulizers.

Unlike freestanding equipment or the like, the proposed nebulizer 1 is preferably designed to be portable, and in particular, is a portable hand-operated device.

The proposed solution may, however, be used not only in the nebulizers 1 specifically described here but also in other nebulizers or inhalers, e.g., powder inhalers or so-called metered dose inhalers.

Preferably, the fluid 2 is a liquid, as already mentioned, especially an aqueous pharmaceutical formulation or an ethanolic pharmaceutical formulation. However, it may also be some other pharmaceutical formulation, a suspension or the like.

According to an alternative embodiment, the fluid 2 may also comprise particles or powder. In this case, instead of the expulsion nozzle 12, some other kind of supply device may be provided, especially an expulsion opening (not shown) or a supply channel (not shown) for supplying the fluid to or powder or the like into the mouthpiece 13. The optional air supply opening 15 then serves to supply ambient air preferably in parallel so as to general or allow an airflow through the mouthpiece 13 with a sufficient volume for breathing in or inhaling.

If necessary, the fluid 2 may also be atomized by means of a propellant gas.

Preferred ingredients and/or formulations of the preferably medicinal fluid 2 are listed, in particular, in WO 2009/115200 A1 and commonly owned, corresponding U.S. Patent Application Publication 2009/0235924, which is incorporated herewith by reference. In particular, these may be aqueous or non-aqueous solutions, mixtures, formulations containing ethanol or free from solvent, or the like.

What is claimed is:

1. Nebulizer for a fluid, comprising:
   a replaceable container containing a fluid,
   a device for counting at least one of the number of containers that have been used and the number of containers that still can be used,
   a device for determining the occurrence of at least one of the following operations:
     opening of the nebulizer for container replacement,
     closure of the nebulizer for completing container replacement,
     reaching or exceed of an allowable number of operations or actuations of the nebulizer for a last container,
     blocking or locking of the nebulizer when no further containers can be inserted,
   and
   an indicator member having a series of numerals for displaying the number counted and at least one symbol for indicating determination of the occurrence of at least one of said at least one operation,
   wherein the indicator member is constructed and arranged for displaying a respective one of said numerals until one of said operations has occurred and for displaying a respective symbol when one of said operations is determined to have occurred.

2. Nebulizer according to claim 1, further comprising a spring positioned to act on the indicator member, wherein the indicator member is moved or rotated stepwise by the force of the spring.

3. Nebulizer according to claim 1, further comprising a lock for preventing operation of the nebulizer, wherein the indicator member drives the lock such that the nebulizer is locked against further use in a first locked state when the container needs to be replaced, and wherein the first locked state is reset by at least one of indexing the indicator member and resetting the lock when the container has been replaced.

4. Nebulizer according to claim 1, wherein the indicator member is adapted to show different or consecutive numbers alternately with a symbol indicating container replacement.

5. Nebulizer according to claim 1, wherein indicator member is adapted to show different or consecutive numbers alternately with a sequence of at least two symbols, wherein a first symbol of the sequence indicates opening of the nebulizer for container replacement and another symbol of the sequence indicates closing of the nebulizer to complete container replacement.

6. Nebulizer according to claim 1, wherein the indicator member is ring-shaped.

7. Nebulizer according to claim 1, wherein the indicator member is mechanically operated for showing said number and symbol.

8. Nebulizer according to claim 1, wherein the indicator member is adapted to show a special end symbol when the nebulizer cannot be used anymore or cannot be used with a further container.

9. Nebulizer according to claim 1, further comprising a housing part which can be opened or separated for replacing the container, and wherein the container is inseparable from the housing part, requiring the housing part to be replaced each time the container is replaced.

10. Nebulizer according to claim 1, wherein the nebulizer is constructed as an inhaler for a medical aerosol treatment.

11. Nebulizer according to claim 1, wherein the indicator only mechanically operable.

12. Nebulizer according to claim 2, wherein the spring is coaxial with the indicator member.

13. Nebulizer for a fluid, comprising:
    a replaceable container containing a fluid,
    a device for counting the number of containers that have been used or still can be used,
    an indicator member displaying said number, and
    a spring member positioned to act on the indicator member,
    wherein the indicator member is moved or rotated stepwise by the force of the spring.

14. Nebulizer according to claim 13, further comprising a lock for preventing operation of the nebulizer, wherein the indicator member drives the lock such that the nebulizer is locked against further use in a first locked state when the container needs to be replaced, and wherein the first locked state is reset by at least one of indexing the indicator member and resetting the lock when the container has been replaced.

15. Nebulizer according to claim 13, wherein the indicator member is ring-shaped.

16. Nebulizer according to claim 15, wherein the spring is coaxial with the indicator member.

17. Nebulizer for a fluid, comprising:
    a replaceable container containing the fluid,
    a device for counting the number of containers that have been used or still can be used,
    an indicator member displaying said number, and
    a lock for preventing operation of the nebulizer,
    wherein the indicator member drives the lock such that the nebulizer is locked against further use in a first locked state when the container needs to be replaced, and wherein the first locked state is resettable by indexing the indicator member when the container has been replaced.

18. Nebulizer according to claim 17, wherein the indicator member is ring-shaped.

19. Nebulizer for a fluid, comprising:
    a replaceable container containing a fluid,
    a lock for locking the nebulizer against further use in a first locked state when a container needs to be replaced, the first locked state being resettable by resetting the lock when the container has been replaced,
    a control member for controlling or driving the lock, and
    a spring adapted for rotating the control member in stepwise manner.

20. Nebulizer according to claim 19, wherein the lock is locked against resetting in a second locked state once a predetermined number of containers has been used or inserted into the nebulizer.

21. Nebulizer according to claim 20, wherein the nebulizer is locked against opening or container replacement by means of the control member in the second locked state.

22. Nebulizer according to claim 19, wherein the nebulizer is locked against opening or container replacement by means of the control member before the first locked state has been reached.

23. Nebulizer according to claim 19, wherein the lock locks the nebulizer in the first locked state against at least one of conveying fluid into a pressure generator, against tensioning of an energy store and a drive spring.

24. Nebulizer according to claim 19, wherein the control member is ring-shaped.

25. Nebulizer for a fluid, comprising:
a replaceable container containing a fluid,
a lock for locking the nebulizer against further use in a first locked state when the container needs to be replaced, the first locked state being resettable by resetting the lock when the container has been replaced, and
a control member for controlling or driving the lock,
wherein the lock is blocked against resetting when in a second locked state once a predetermined number of containers has been used or inserted into the nebulizer.

26. Nebulizer according to claim 25, wherein the control member is ring-shaped.

27. Nebulizer according to claim 25, wherein the control member forms an indicator member for displaying at least one of the number of containers that have been used, the number of containers that still can be used, and a symbol indicating the need for container replacement.

28. Nebulizer according to claim 27, wherein the indicator member shows a symbol indicating the need for container replacement.

29. Nebulizer according to claim 25, wherein the control member is adapted to block at least one of opening of the nebulizer and container replacement until a predetermined number of operations has been reached or exceeded.

30. Nebulizer according to claim 25, wherein the control member is adapted to block at least one of opening of the nebulizer and container replacement until a predetermined number of operations has been reached or exceeded.

31. Nebulizer according to claim 25, wherein the nebulizer is locked against opening or container replacement by means of the control member before the first locked state has been reached.

32. Nebulizer according to claim 25, wherein the nebulizer is locked against opening or container replacement by means of the control member in the second locked state.

33. Nebulizer according to claim 25, wherein the lock locks the nebulizer in the first locked state against at least one of conveying fluid into a pressure generator tensioning of an energy store and tensioning of a drive spring of the nebulizer.

34. Nebulizer according to claim 33, further comprising a securing device preventing a used container from being connected to the nebulizer.

35. Nebulizer according to claim 32, wherein the securing device comprises locking portions on the which move radially or are force apart after the used container is detached from the nebulizer.

36. Nebulizer for a fluid, comprising:
a replaceable container containing a fluid, and
a housing part which can be detached or opened for replacing the container, and
a securing device associated with the container for preventing a used container from being connected to the nebulizer,
wherein the securing device comprises locking portions that are moveable radially at least after the used container has been detached from the nebulizer such that the used container cannot be re-connected to the nebulizer.

37. Nebulizer according to claim 36, wherein the locking portions are arm-shaped.

38. Nebulizer according to claim 36, wherein the locking portions are at least partly biased in a radial direction.

39. Nebulizer according to claim 36, wherein the locking portions are held against moving radially by a securing part.

40. Nebulizer according to claim 39, wherein the securing part is ring-shaped.

41. Nebulizer according to claim 40, wherein the securing part is movable into a position to free the locking portions when at least one of the container is inserted for the first time and when completely closing the nebulizer or a housing part thereof.

42. Nebulizer according to claim 36, wherein the securing device is formed of a stamped and unitary part.

43. Nebulizer according to claim 36, wherein the locking portions are made of metal.

44. Nebulizer according to claim 36, wherein the securing device is adapted to at least one of prevent detachment of the container from the housing part and prevent reconnection of the housing part to the nebulizer when the housing part has been previously connected.

45. Nebulizer according to claim 36, wherein the securing device is adapted to inseparably hold the container in the housing part, and wherein the container is moveable back and forth within the nebulizer relative to the housing part during at least one of conveying of the fluid, pressure generation and nebulization.

46. Nebulizer according to claim 36, wherein the securing device forms a transportation lock for holding the container fixed in the nebulizer in a delivery state, and wherein the transportation lock is openable during or after connection of the container or housing part to the nebulizer.

47. Nebulizer according to claim 36, further comprising a counter device located at the housing part.

48. Nebulizer according to claim 47, wherein the counter device is adapted to actuate or trigger at least one of locking of the nebulizer against at least one further use, movement or rotation of the indicator or control member, and actuation of a locking member.

49. Nebulizer according to claim 36, wherein the housing part is provided with a coding such that the housing part is mountable to the nebulizer only if the coding matches to a complementary coding arranged at the nebulizer.

50. Nebulizer according to claim 49, wherein the coding is formed at the housing part by at least one coding element that is attached to the housing part by at least one of clipping and inserting.

51. Nebulizer according to claim 36, wherein the locking portions are moveable radially outward at least after the used container has been detached from the nebulizer such that the used container cannot be re-connected to the nebulizer.

52. Nebulizer for a fluid, comprising:
a replaceable container containing a fluid,
a device for counting at least one of the number of containers that have been used and the number of containers that still can be used, and
an indicator member having a series of numerals for displaying said numbers and at least one symbol for indicating container replacement,
wherein the indicator member is adapted to show different numerals alternately with the at least one symbol indicating container replacement.

53. Nebulizer for a fluid, comprising:
a replaceable container containing a fluid,
a device for counting at least one of the numbers of containers that have been used and the numbers of containers that still can be used, and
an indicator member having a series of numerals for indicating said numbers and at least two symbols of which a first symbol indicates opening of the nebulizer for container replacement and a second symbol indicates closing of the nebulizer to complete container replacement,
wherein indicator member is adapted to show different numerals alternately with a sequence of said first and second symbols.

54. Nebulizer according to claim 52, wherein the indicator member is moved or rotated stepwise by the force of a spring.

55. Nebulizer according to claim 53, wherein the indicator member is moved or rotated stepwise by the force of a spring.

56. Nebulizer according to claim 52, wherein the indicator member drives a lock such that the nebulizer is locked against further use in a first locked state when the container needs to be replaced, and wherein the first locked state is reset by at least one of indexing the indicator member and resetting the lock when the container has been replaced.

57. Nebulizer according to claim 53, wherein the indicator member drives a lock such that the nebulizer is locked against further use in a first locked state when the container needs to be replaced, and wherein the first locked state is reset by at least one of indexing the indicator member and resetting the lock when the container has been replaced.

58. Nebulizer according to claim 52, wherein the indicator member is mechanically operated for showing said numerals and symbols.

59. Nebulizer according to claim 53, wherein the indicator member is mechanically operated for showing said numerals and symbols.

* * * * *